(12) United States Patent
Little et al.

(10) Patent No.: US 11,185,460 B2
(45) Date of Patent: Nov. 30, 2021

(54) SELF CONTAINED POWERED EXOSKELETON WALKER FOR A DISABLED USER

(71) Applicant: REX BIONICS LIMITED, Auckland (NZ)

(72) Inventors: Richard Little, North Shore (NZ); Robert Alexander Irving, Manukau (NZ)

(73) Assignee: REX BIONICS LIMITED, Auckland (NZ)

(*) Notice: Subject to any disclaimer, the term of this patent is extended or adjusted under 35 U.S.C. 154(b) by 403 days.

(21) Appl. No.: 14/850,349

(22) Filed: Sep. 10, 2015

(65) Prior Publication Data

US 2016/0067137 A1 Mar. 10, 2016

Related U.S. Application Data

(63) Continuation of application No. 12/801,809, filed on Jun. 25, 2010, now abandoned.

(51) Int. Cl.
*A61H 3/00* (2006.01)
*A61H 1/02* (2006.01)
(Continued)

(52) U.S. Cl.
CPC .............. *A61H 3/00* (2013.01); *A61F 2/72* (2013.01); *A61H 1/0255* (2013.01);
(Continued)

(58) Field of Classification Search
CPC .......... B25J 9/0006; A61H 3/00; A61H 3/008; A61H 2003/005; A61H 2003/007;
(Continued)

(56) References Cited

U.S. PATENT DOCUMENTS

| 777,137 A | 12/1904 | Pickles |
| 5,252,102 A * | 10/1993 | Singer .................... A61F 2/68 623/24 |

(Continued)

FOREIGN PATENT DOCUMENTS

| GB | 2301776 | 12/1996 |
| JP | 2005-237504 A | 9/2005 |

(Continued)

OTHER PUBLICATIONS

Canadian Office Action dated Dec. 19, 2019 (5 pages).

*Primary Examiner* — Michael J Tsai
(74) *Attorney, Agent, or Firm* — Jacobson Holman PLLC

(57) ABSTRACT

A walker for use by a mobility impaired disabled user. The walker supports the user while moving them through a set of movements correlating to a walking motion. The walker includes an exoskeleton, a power source in the form of a battery pack or other similar onboard power pack together with its associated power supply cables, and a control system The exoskeleton includes a rigid pelvic support member including a pelvic harness and a pair of leg structures. Each of the leg structures comprise an upper leg structural member, a lower leg structural member, a foot member, a main hip actuator, a knee actuator and a main foot actuator.

29 Claims, 42 Drawing Sheets

(51) Int. Cl.
   *B25J 9/00* (2006.01)
   *A61F 2/72* (2006.01)
   *A61F 2/70* (2006.01)

(52) U.S. Cl.
   CPC .......... *A61H 1/0266* (2013.01); *B25J 9/0006* (2013.01); *A61F 2002/701* (2013.01); *A61H 3/008* (2013.01); *A61H 2201/1215* (2013.01); *A61H 2201/163* (2013.01); *A61H 2201/164* (2013.01); *A61H 2201/165* (2013.01); *A61H 2201/1621* (2013.01); *A61H 2201/1635* (2013.01); *A61H 2201/1642* (2013.01); *A61H 2201/1676* (2013.01); *A61H 2201/5058* (2013.01)

(58) Field of Classification Search
   CPC .... A61H 1/0237; A61H 1/024; A61H 1/0244; A61H 1/0262; A61H 2001/0248; A61H 2201/1215; A61H 2201/1238; A61H 2201/164; A61H 2201/165; A61H 2201/1652
   See application file for complete search history.

(56) References Cited

U.S. PATENT DOCUMENTS

| | | | |
|---|---|---|---|
| 5,282,460 A | 2/1994 | Boldt | |
| 5,476,441 A | 12/1995 | Durfee | |
| 5,749,668 A * | 5/1998 | McIlvain | A63B 21/154 482/79 |
| 5,961,541 A | 10/1999 | Ferrati | |
| 7,153,242 B2 | 12/2006 | Goffer | |
| 7,190,141 B1 | 3/2007 | Ashrafiuon | |
| 7,429,253 B2 | 9/2008 | Shimada et al. | |
| 7,731,673 B2 | 6/2010 | Hiki | |
| 2003/0093021 A1* | 5/2003 | Goffer | A61F 5/0102 602/23 |
| 2004/0172097 A1* | 9/2004 | Brodard | A61H 1/0255 607/49 |
| 2005/0090954 A1 | 4/2005 | Mansell et al. | |
| 2006/0064047 A1 | 3/2006 | Shimada | |
| 2006/0200272 A1 | 9/2006 | Kawai | |
| 2006/0260620 A1* | 11/2006 | Kazerooni | A61B 5/1038 128/845 |
| 2007/0016329 A1 | 1/2007 | Herr et al. | |
| 2007/0043449 A1 | 2/2007 | Herr et al. | |
| 2007/0123997 A1 | 5/2007 | Herr | |
| 2007/0162152 A1 | 7/2007 | Herr et al. | |
| 2007/0241713 A1* | 10/2007 | Yamamoto | B62D 57/032 318/568.12 |
| 2008/0154165 A1* | 6/2008 | Ashihara | A61F 5/0102 602/23 |
| 2009/0210093 A1* | 8/2009 | Jacobsen | A61H 3/008 700/260 |

FOREIGN PATENT DOCUMENTS

| | | |
|---|---|---|
| JP | 2007-307216 A | 11/2007 |
| WO | 2007/088044 | 8/2007 |
| WO | 2009/082249 A2 | 7/2009 |

* cited by examiner

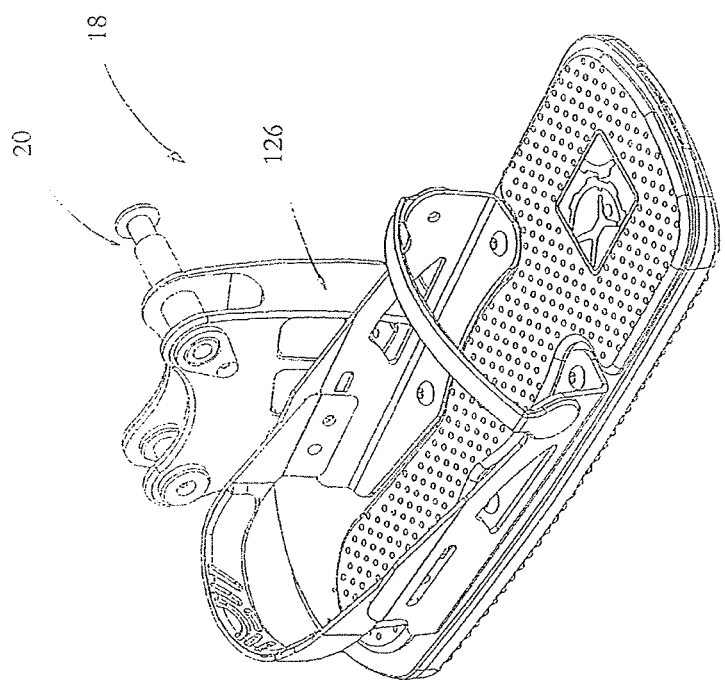
FIGURE 10a
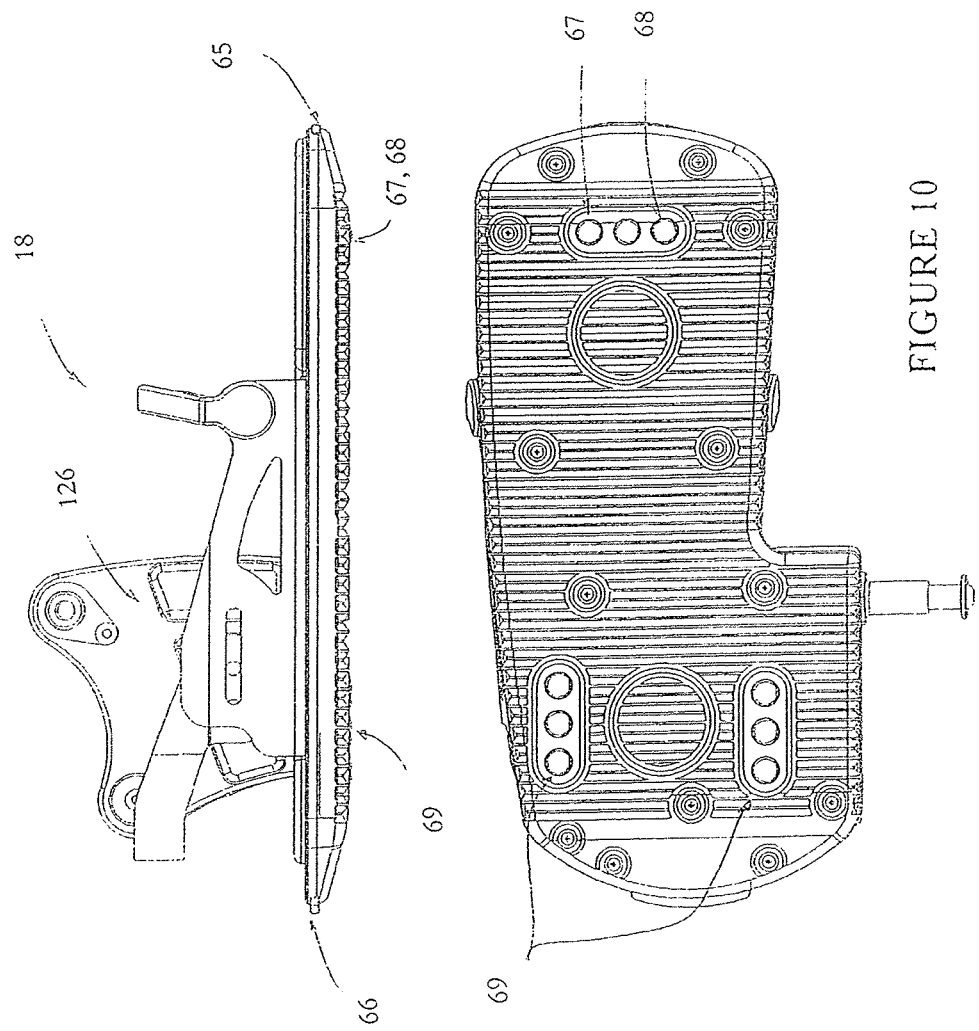
FIGURE 9
FIGURE 10

C   C

SELF CONTAINED POWERED EXOSKELETON WALKER FOR A DISABLED USER

FIELD OF INVENTION

The present invention relates to a self contained powered exoskeleton walker for a disabled user that at least substitutes fully disabled functions of a user required for walking. In particular but not solely the present invention relates to a robotic exoskeleton that a paraplegic person is fully supportable by, in an upright condition to effect a walking gait.

BACKGROUND

During a walking stride by a non disabled person, the centre of mass of their body weight tends to move loosely between being almost directly above one foot, to being above the other foot, in a side to side reciprocating movement of their body weight. This side to side reciprocation of the body weight is minimised by having the feet extend inwardly to almost directly beneath the person's hips, to allow a smoother walking motion. Whatever instability a non disabled person has during walking may be made up for by the speed of reaction and stabilising input of other muscles such as abdominal and back muscles.

A walking gait disabled person such as a paraplegic person, does not have the ability to walk. They may be wheel chair bound and sedentary for much of the time. Lack of movement of the legs of a paraplegic person is known to cause a number of complications. Many are spinal injured and hence together with muscle wastage and lack of circulation in the limbs and abdomen due to being seated, complications arise. These can include skin problems such as pressure sores, bladder infections, deep vein thrombosis and contracture. Limb movement is one way by which complications can be avoided or their instances reduced. For example, circulation can be improved by the person being in a standing position. Applying some pressure to a person's bones by virtue of being in a standing position and allowing their legs to receive some of their bodyweight is also beneficial.

Accordingly it is an object of the present invention to provide a self contained powered exoskeleton walker for a disabled user that at least substitutes fully disabled functions of a user required for walking that overcomes the above-mentioned shortfalls and/or hat will at least provide the public with a useful choice.

BRIEF DESCRIPTION OF THE INVENTION

According to one aspect, the invention may be said to broadly be said to be a self contained powered exoskeleton walker for a disabled user that at least substitutes fully disabled functions of a user required for walking, said walker comprising:
i) an exoskeleton comprising:
  a. a rigid pelvic support member carrying a user securing arrangement for securely fastening a user to at least the pelvic support member and to vertically support said user relative to said exoskeleton,
  b. a first leg structure and a second leg structure, each of the first leg structure and the second leg structure being coupled to and extending from said pelvic support member for operational location adjacent a respective leg of a user, each of the first leg structure and second leg structure comprising
    an upper leg structural member for engagement with the upper leg of the user, the upper leg structural member being pivotally engaged at a first end thereof to the pelvic support member by a hip joint, wherein the hip joint is configured for facilitating the multi axis rotational movement of said upper leg structural member relative to said pelvic support member (i) towards and away from the coronal plane of the body of the user and (ii) toward and away from the sagittal plane of the body of the user for adduction and abduction;
    a lower leg structural member for engagement with the lower leg of the user, the lower leg structural member being pivotally engaged at a first end thereof to a second end of the upper leg structural member by a knee joint,
    a foot member for engagement with the foot of a user, the foot member being pivotally engaged to a second end of the lower leg member by a foot joint,
    a main hip actuator configured for actuating pivotal movement of said upper leg structural member relative to said pelvic support member about said hip joint, to in use pivot the upper leg structural member towards and away from the coronal plane of the body of the user,
    a secondary hip actuator, configured for actuating pivotal movement of said upper leg structural member relative the pelvic support member about said hip joint towards and away from the sagittal plane of the body of the user for adduction and abduction,
    a knee actuator configured for actuating pivotal movement of said lower leg structural member relative said upper leg structural member about said knee joint,
    a main foot actuator configured for actuating pivotal movement of said foot member relative said lower leg structural member about said foot joint about an axis of rotation substantially parallel to the axis of rotation of the knee joint;
ii) a power source configurable for providing power to at least one or more selected from said main hip actuators, knee actuators, and main foot actuators,
iii) a control system configurable for controlling movement of at least one or more selected from said main hip actuators, knee actuators, and main foot actuators, thereby to move the exoskeleton relative to the ground on which the walker is positioned, for at least the purposes of effecting a walking motion to said user, and
iv) wherein in at least one or more selected from the length of each upper leg structural member and the length of each lower leg structural member, is adjustable to vary the distance between the hip joint and knee joint and the distance between foot joint and knee joint, respectively.

Preferably said secondary hip actuator is configured for actuating said pivotal movement of said upper leg structural member to either side of a plane parallel to the sagittal plane and passing through said hip joint and preferably in a range of about ten degrees each side.

Preferably said hip joint is one selected from a rose joint, universal joint or ball and socket joint, configured for facilitating the multi axis rotational capability of said upper leg structural member relative to said pelvic support member.

Preferably said walker is configured to at least partially prevent pivoting movement of the upper leg structural member about its longitudinal axis.

Preferably pivotal movement of the upper leg structural member towards and away from the coronal plane of the body of the user is about an axis of rotation extending downwardly away from said sagittal plane at an angle of between 1 and 6 degrees and preferably 4 degrees to the transverse plane.

Preferably the knee joint is offset rearwardly from the upper leg structural member to align substantially with an axis of rotation of a user's knee in operation.

Preferably the knee joint is a polycentric knee joint.

Preferably said foot joint is a rose joint, a universal joint or ball and socket joint, configured for facilitating the multi axis rotational capability of said foot member relative said lower leg structural member.

Preferably said exoskeleton comprises, for each of the first leg structure and second leg structure, a secondary foot actuator, configured for actuating rotation of said foot member in towards and away from said sagittal plane about said foot joint.

Preferably each foot joint is configured with its axis of rotation about the anterior/posterior plane extending downwardly in a lateral direction at an angle of between zero and 6 degrees.

Preferably pivotal movement of the foot member towards and away from the coronal plane of the body of the user is about an axis of rotation extending downwardly away from said sagittal plane at an angle of between 1 and 6 degrees and preferably 4 degrees to the transverse plane.

Preferably each of said upper leg structural member and lower leg structural member include a fastener to fasten to the legs of a user.

Preferably each said fastener comprise an orthotic device affixed to a sid upper leg structural member and lower leg structural member and that is shaped to receive the rear part of the users legs and a strap to hold said leg to said orthotic device.

Preferably said fasteners comprises an adjustable webbing or strapping for securing at least partially about a user's leg.

Preferably said adjustable webbing includes an adjustable fastening arrangement.

Preferably each of said upper leg structural members has engaged thereto an upper leg orthotic device to facilitate the upper leg of a user, in use, being rigidly held relative a respective said upper leg structural member and wherein each said lower leg structural member has engaged thereto a lower leg orthotic device to facilitate the lower leg of a user, in use, being rigidly held relative a respective said lower leg structural member.

Preferably each of said upper leg orthotic devices each carry at least one strap to secure said upper leg to said orthotic device and each said lower leg orthotic device carries at least one strap to secure said lower leg to said orthotic device.

Preferably said orthotic devices are C-shaped, and said pelvic support member is substantially C-shaped and presented to allow engagement of the exoskeleton with a person by relative movement in a direction normal to the coronal plane.

Preferably the length of each upper leg structural members can be varied to vary the distance between the hip joint and knee joint.

Preferably each said upper leg structural member comprises at least two parts that are movable relative each other to extend and contract the effective length of the upper leg structural member.

Preferably the two parts of said upper leg structural member are, by virtue of (a) a threaded relationship, (b) a telescopic relationship or (c) sliding relationship to each other, adjustable in length.

Preferably the upper leg structural member is configured for removably receiving an upper leg lengthening insert to allow an extending and contracting of the effective length of the upper leg structural member.

Preferably the upper leg lengthening insert is securable to the upper leg structural member by one or more selected from a thread formation, a bayonet-type formation, a snap fit formation, or the like.

Preferably the length of each lower leg structural members can be varied to vary the distance between the foot joint and knee joint.

Preferably each said lower leg structural member comprises at least two parts that are movable relative each other to extend and contract the effective length of the lower leg structural member.

Preferably the two parts of said lower leg structural member are, by virtue of (a) a threaded relationship, (b) a telescopic relationship or (c) sliding relationship to each other, adjustable in length.

Preferably the lower leg structural member is configured for removably receiving a lower leg lengthening insert to allow an extending and contracting of the effective length of the lower leg structural member.

Preferably the lower leg lengthening insert is securable to the lower leg structural member by one or more selected from a thread formation, a bayonet-type formation, a snap fit formation, or the like.

Preferably a user is fully supported by a user securing arrangement at or towards the pelvic region of the user, so that that the user's legs do not support the weight of the user.

Preferably the user securing arrangement includes one or more selected from
 i) a pelvic harness suitable for securing a user's pelvis to the pelvic support member;
 ii) a packing arrangement for snugly fitting a user's hips against the pelvic support member; and
 iii) a fastener arrangement for securing each of the user's legs to an associated leg structure.

Preferably the packing arrangement is an inflatable pressure vessel.

Preferably the packing arrangement is at least one foam cushion.

Preferably said exoskeleton includes a torso support that, in use engages to a user above said user securing arrangement.

Preferably the torso support is secured to said rigid pelvic support member and includes a rigid member extending upward from said rigid pelvic support member and at least one fastener (preferably a fastener strap) to capture the torso of the user to or toward the rigid member.

Preferably the user is suspended from the rigid pelvic support member by a pelvic harness.

Preferably said pelvic harness is affixed to said pelvic support member.

Preferably said pelvic harness includes two thigh traps, one for each thigh of the user and to locate about each tight in a snug manner, each said thigh strap including a take-off strap via which an upward support force can be applied to the thigh that is carried by the pelvic support member.

Preferably said take-off strap projects in use upwardly from said thigh strap at a side of the thigh of the user that is opposite to the sagittal plane of the user in order to provide an upwards support force to the thigh of the user that discourages the thigh strap from migrating up into the crutch of the user.

Preferably said pelvic harness comprises a buttock cradle that includes two staps, one to locate against the buttocks of a user at a lower region thereof and one to locate against the buttocks of a user at a higher more region thereof.

Preferably said two buttock straps are affixed to at least two suspension straps that are connected to said pelvic support harness and via which at least some of the weight of the person carried by said pelvic harness can be transferred to said pelvic support member.

Preferably the pelvic harness includes a waist strap that locates at least partly around the hips or waist of a user and is connected to said pelvic support member to hold said user relative to said pelvic support member and restrict movement of the user in a direction towards and away from the coronial plane relative to said pelvic support member.

Preferably said pelvic support member includes a C-shaped user interface surface that is presented to locate predominantly about the posterior side of the hip and/or waist region of the user.

Preferably said user interface projects to be located at at least part of each side of said user also.

Preferably a pelvic harness is suspended from said pelvic support member, said pelvic harness to locate about the user in a manner to vertically support said user, wherein said pelvic harness includes at least one pocket that can removably receive a packer of an appropriate shape and size to provide packing intermediate of said user and said pelvic support member.

Preferably the user interface surface is shaped to snugly locate adjacent the user and said packers can fill space between said user and said user interface.

Preferably a plurality of sensors are provided for providing information to the control system for facilitating the control of movement of the exoskeleton.

Preferably the plurality of sensors are configured for sensing a characteristic to be sensed, and generating a signal indicative of that characteristic, and transmitting the signal to the control system for facilitating the control of movement of the exoskeleton.

Preferably said sensors are selected from at least one of:
i) an accelerometer to measure the acceleration of at least one or more selected from said pelvic support member, the upper leg structural members, the lower leg structural members and the foot members,
ii) an inclinometer to measure the inclination of at least one or more selected from said pelvic support member, the upper leg structural members, the lower leg structural members and the foot members,
iii) distance sensors configured for determining the slope of the ground anteriorly, posteriorly and laterally of the walker,
iv) pressure sensors disposed on the foot member to determine the pressure being applied by the foot member to the ground, and
v) position sensors for determining the position and velocity of the actuators.

Preferably said controller includes a gyroscope configured for defining a reference frame for the purposes of positional control of the or part of the exoskeleton.

Preferably said walker includes a human interface device that preferably includes at least one of a joystick and a keypad.

Preferably the exoskeleton is configurable into a sitting position for facilitating the transfer of a user to and from the walker, said exoskeleton comprising support surfaces configured and dimensioned to be engageable by a user for facilitating transfer of the user to and/or from the walker when in the sitting position.

Preferably the support surfaces are hand holds configured to extend substantially horizontally when the walker is in the sitting position.

Preferably the support surfaces are defined by covers that cover at least part of the exoskeleton.

In a second aspect the present invention may be said to be an exoskeleton device worn by a paraplegic user for device controlled walking of the user, said exoskeleton device comprising:
a. a rigid pelvic support member carrying a user securing arrangement to engage with the user at their pelvis to vertically support the user relative to said exoskeleton,
b. a first leg structure and a second leg structure, each of the first leg structure and the second leg structure being coupled to and extending from said pelvic support member for operational location adjacent a respective leg of a user, each of the first leg structure and second leg structure comprising
an upper leg structural member for engagement with the upper leg of the user, the upper leg structural member being pivotally engaged at a first end thereof to the pelvic support member by a hip joint, wherein the hip joint is configured for facilitating the multi axis rotational movement of said upper leg structural member relative to said pelvic support member towards and away from the coronal plane of the body of the user;
a lower leg structural member for engagement with the lower leg of the user, the lower leg structural member being pivotally engaged at a first end thereof to a second end of the upper leg structural member by a knee joint,
a foot member for engagement with the foot of a user, the foot member being pivotally engaged to a second end of the lower leg member by a foot joint,
a main hip actuator configured for actuating pivotal movement of said upper leg structural member relative to said pelvic support member about said hip joint, to in use pivot the upper leg structural member towards and away from the coronal plane of the body of the user,
a knee actuator configured for actuating pivotal movement of said lower leg structural member relative said upper leg structural member about said knee joint,
a main foot actuator configured for actuating pivotal movement of said foot member relative said lower leg structural member about said foot joint about an axis of rotation substantially parallel to the axis of rotation of the knee joint; and
wherein in at least one or more selected from the length of each upper leg structural member and the length of each lower leg structural member, is adjustable to vary the distance between the hip joint and knee joint and the distance between foot joint and knee joint, respectively Preferably said exoskeleton comprises a power source configurable for providing power to at least one or more selected from said main hip actuators, knee actuators, and main foot actuators.

Preferably the exoskeleton device is worn by a paraplegic user for device controlled and user specified walking motion.

Preferably the user securing arrangement vertically supports all of the user relative to said exoskeleton.

Preferably the hip joint is configured for facilitating the multi axis rotational movement of said upper leg structural member relative to said pelvic support member toward and away from the sagittal plane of the body of the user for adduction and abduction and a secondary hip actuator is provided, configured for actuating pivotal movement of said upper leg structural member relative the pelvic support member about said hip joint towards and away from the sagittal plane of the body of the user for adduction and abduction.

Preferably a power source is provided configurable for providing power to at least one or more selected from said main hip actuators, knee actuators, and main foot actuators, Preferably a control system is provided configurable for controlling movement of at least one or more selected from said main hip actuators, knee actuators, and main foot actuators, thereby to move the exoskeleton relative to the ground on which the walker is positioned, for at least the purposes of effecting a walking motion to said user.

In yet a further aspect herein described may be said to be an exoskeleton suitable for a walking aid or a medical device, said exoskeleton comprising:
  i) a rigid pelvic support member suitable for snug engagement with a user's hips operationally
  ii) a user securing arrangement to securely fastening a user at least to the pelvic support member to support said user operationally;
  iii) a first leg structure and a second leg structure, each of the first leg structure and the second leg structure being coupled to and extending from said pelvic support member for operational location adjacent a respective leg of a user, each of the first leg structure and second leg structure comprising
    a. an upper leg structural member for engagement with the upper leg of the user, the upper leg structural member being pivotally engaged at a first end thereof to the pelvic support member by a hip joint wherein the hip joint is configured for facilitating the multi axis rotational capability of said upper leg structural member relative to said pelvic support member for movement towards and away from the coronal plane and for abduction and adduction,
    b. a lower leg structural member for engagement with the lower leg of the user, the lower leg structural member being pivotally engaged at a first end thereof to a second end of the upper leg structural member by a knee joint,
    c. a foot member for engagement with the foot of a user, the foot member being pivotally engaged to a second end of the lower leg member by a foot joint,
    d. a main hip actuator configured for actuating rotation of said upper leg structural member relative to said pelvic support member about said hip joint, to in use pivot the upper leg structural member towards and away from the coronal plane,
    e. a secondary hip actuator, configured for actuating rotation of said upper leg structural member for adduction or abduction about said pelvic support member,
    f. a knee actuator configured for actuating rotation of said lower leg structural member relative said upper leg structural member about said knee joint, and
    g. a main foot actuator configured for actuating rotation of said foot member relative said lower leg structural member about said foot joint about an axis of rotation substantially parallel to the axis of rotation of the knee joint.

Preferably the user securing arrangement includes
  i) a pelvic harness securable about a user's pelvis and affixed to the pelvic support member to suspend the user thereby, and
  ii) securing fasteners suitable for securing a user's legs to the leg structures operationally.

Preferably the knee joint is a polycentric knee joint.

Preferably the exoskeleton is a gait vehicle to carry a bipedal locomotion disabled user.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

The term "anterior" as used in this specification relates to a direction corresponding to the front or in front of a human user, and the term "anteriorly" is to be construed accordingly.

The term "posterior" as used in this specification relates to a direction corresponding to the back of or behind a human user, and the term "posteriorly" is to be construed accordingly.

As used herein the term "and/or" means "and" or "or", or both.

As used herein "(s)" following a noun means the plural and/or singular forms of the noun.

BRIEF DESCRIPTION OF THE DRAWINGS

FIG. 9 shows a side view of a foot member, FIG. 10 shows a bottom view of a foot member, FIG. 10a shows a perspective view of a foot member.

DETAILED DESCRIPTION OF PREFERRED EMBODIMENTS

Figure 1:
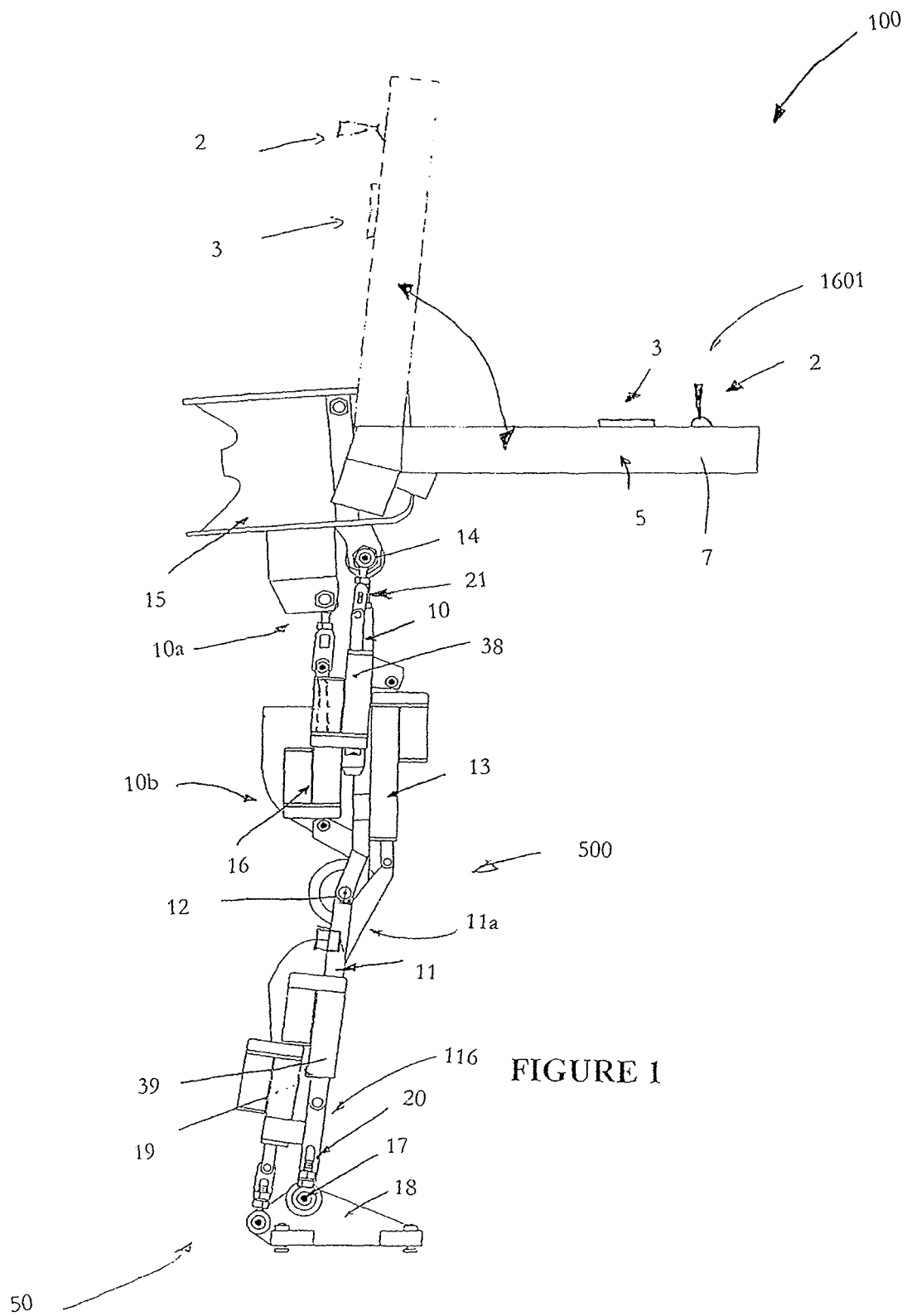
FIG. 1 shows a side view of the exoskeleton forming part of the walker of the present invention with orthotics provided, shown in this embodiment without a secondary hip actuator.

The current invention relates to a walker that includes an exoskeleton which in effect completely supports and guides the dead weight of a user's body and can move around in a walking gait like manner. It is envisaged that a user of this device may have limited strength, and or movement of their arms. For this reason, the user's arms need not be relied upon to support themselves (for example by means of crutches).

With reference to the above drawings, in which similar features are generally indicated by similar numerals, a walker is generally indicated by the numeral 100.

The walker comprises an exoskeleton suitable for use to control and determine the walking gait of a disabled user and is generally indicated by the numeral 500.

The walker 100 is suitable for fully supporting a mobility impaired disabled user while moving through a set of movements correlating to a walking gait. Broadly speaking, the walker 100 preferably comprises an exoskeleton 500, a power source in the form of a battery pack or other similar onboard power pack (not shown) together with its associated power supply cables (not shown), and a control system (not shown).

The exoskeleton 500 comprises a rigid pelvic support member 15 including a pelvic harness 96, and a pair of leg structures 50 (a first leg structure and second leg structure).

The pelvic support member 15 is required to be of a relatively low weight, while having a high rigidity in operation. For this reason, the pelvic support member 15 may be moulded from carbon fibre as a single unit having an interior hollow space (not shown). It is envisaged that the pelvic support member 15 could also be moulded from glass fibre. The pelvic support member 15 further includes transverse shear webs extending across its interior hollow space. It is preferably C-shaped so that it can be engaged around a users pelvis by engagement from in a direction towards the coronal plane of the user (where the user is in an upright position).

Each of the leg structures 50 comprise an upper leg structural member 10, a lower leg structural member 11, a foot member 18, a main hip actuator 16, a knee actuator 13 and a main foot actuator 19. More detail of examples are described below.

The upper leg structural member 10 is provided for securing with an upper leg 610 of a user 600, the upper leg structural member 10 being pivotally engaged at a first end 10a thereof to the pelvic support member 15 by the hip joint 14.

The lower leg structural member 11 is provided for securing with the lower leg 620 of the user 600, the lower leg structural member 11 being pivotally engaged at a first end 11a thereof to a second end 10b of the upper leg structural member 10 by a knee joint 12.

In one embodiment, it is envisaged that the knee joint 12 will only allow relative pivotal movement between the upper leg structural member 10 and the lower leg structural member 11 along a single plane. It will preferably use a roller bearing arrangement (not shown) to accomplish this. However, the knee joint 12 may be subject to large twisting forces or sideways forces, causing axial forces on the roller bearing arrangement. For this reason, it is envisaged that the knee joint will also include a thrust bearing arrangement (not shown) configured for resisting axial forces on the knee joint 12.

The knee joint may be a polycentric knee joint.

Each of said upper leg structural member 10 and lower leg structural member 11 include a fastening arrangement such as in the form of adjustable fasteners 46 for fastening the respective leg structures 50 with the associated legs of a user 600 in use. It is envisaged that the fasteners 46 may be comprised of flexible webbing or straps, and can include an adjustable fastening arrangement 47, which could be in the form of straps having a hook and loop fastening system such as Velcro® which pass through a buckle. Alternately, the adjustable fastening arrangement can include a typical buckle, ratchet buckle or catch formation.

The foot member 18 is for locating the foot 630 of a user 600, the foot member 18 being pivotally engaged to a second end lib of the lower leg structural member 11 by a foot joint 17. Each of said foot members 18 includes a foot member structural component 126 for guiding the movement of a user's feet 630 operationally.

In one embodiment, each of said foot members 18 may include a designated shoe 31 which is conveniently removably engagable with the foot member structural component 126, and into which the user 600 can place their feet. The shoe 31 may be removably engagable with the foot member structural component 126 by a securing formation, such as a clip-type formation, a snap-fit type formation, a bayonet-type formation or any other suitable formation. The position of the shoe 31 relative to the foot member structural component 126 is envisaged as being adjustable, to allow the alignment of a user's ankle with the axis of rotation 17A of the foot joint 17.

In another embodiment, each of the foot members 18 include a foot engaging formation 34 for receiving the users own shoe and in that way locating a user's foot 630. The foot engaging formation 34 is coupled to the foot member structural component 126 in an adjustable manner, to again allow for positioning of the user's 600 ankle.

The main hip actuator 16 is configured for actuating rotation of said upper leg structural member 10 relative to said pelvic support member 15 about said hip joint 14, to thereby (in use) pivot the upper leg structural member 10 in towards and away from the coronal plane of the user 600.

The exoskeleton 500 may further include, for each of the leg structures 50, a secondary hip actuator 38. The secondary hip actuator 38 is configured for actuating rotation of the upper leg structural member 10 in adduction and abduction relative the pelvic support member 15 and relative to the user 600 in use. In a preferred embodiment, the secondary hip actuator 38 is configured for actuating rotation of said upper leg structural member 10 in towards and away from a plane passing through the hip joint and parallel to the sagittal plane, in a range of about twelve degrees, and more preferably about six degrees, to either side of the plane.

The knee actuator 13 is configured for actuating rotation of said lower leg structural member 11 relative said upper leg structural member 10 about said knee joint 12.

The main foot actuator 19 is configured for actuating rotation of said foot member 18 relative said lower leg structural member 11 about said foot joint 17 about an axis of rotation 17A substantially parallel to the axis of rotation 12A of the knee joint 12.

Further, the exoskeleton 500 may include for each of the leg structures 50 a secondary foot actuator 39. The secondary foot actuator 39 is configured for actuating rotation of said foot member 18 in towards and away from the sagittal plane about said foot joint 17. The rotation may be in the range of about ten degrees, and more preferably about six degrees to either side.

The actuators used are preferably low voltage DC actuators with position feedback through a sensor in the actuator. The low voltage aspect of the actuator is important in that it is safe for use and will do no harm to the user in the case of a fault. Typically, an actuator would be caused to move by an electric motor (not shown) driving a worm gear (not shown), which in turn causes the actuator to extend or retract.

In use, the user is strapped to and supported by the exoskeleton 500. It is envisaged that the walker 100 is a self contained, and in use, self supporting structure that is capable of moving the user 600 over ground. It does so by moving the legs of the user in a walking gait like manner and supporting the user during the movement. The walker 100 includes a user fastening arrangement that may comprise a pelvic harness 96 including braces, tethers, strapping, a harness or webbing to hold the user's 600 hips snugly to the pelvic support member 15, and either orthotics or adjustable fasteners to secure the user's legs and/or feet to the leg structures 50. The braces include orthotics 4 positioned, configured and designed to ensure correct alignment of the users limbs and joints and can also include straps or webbing. The orthotics help ensure the user 600 is not only supported but is also correctly aligned within the exoskeleton so as not to damage the user's 600 limbs or joints. The orthotics may include webbing or straps to hold the user in position relative the formed portion of the orthotics. The webbing may also facilitate an easy and adjustable fitting and release of the user from the walker 100.

Figure 3:
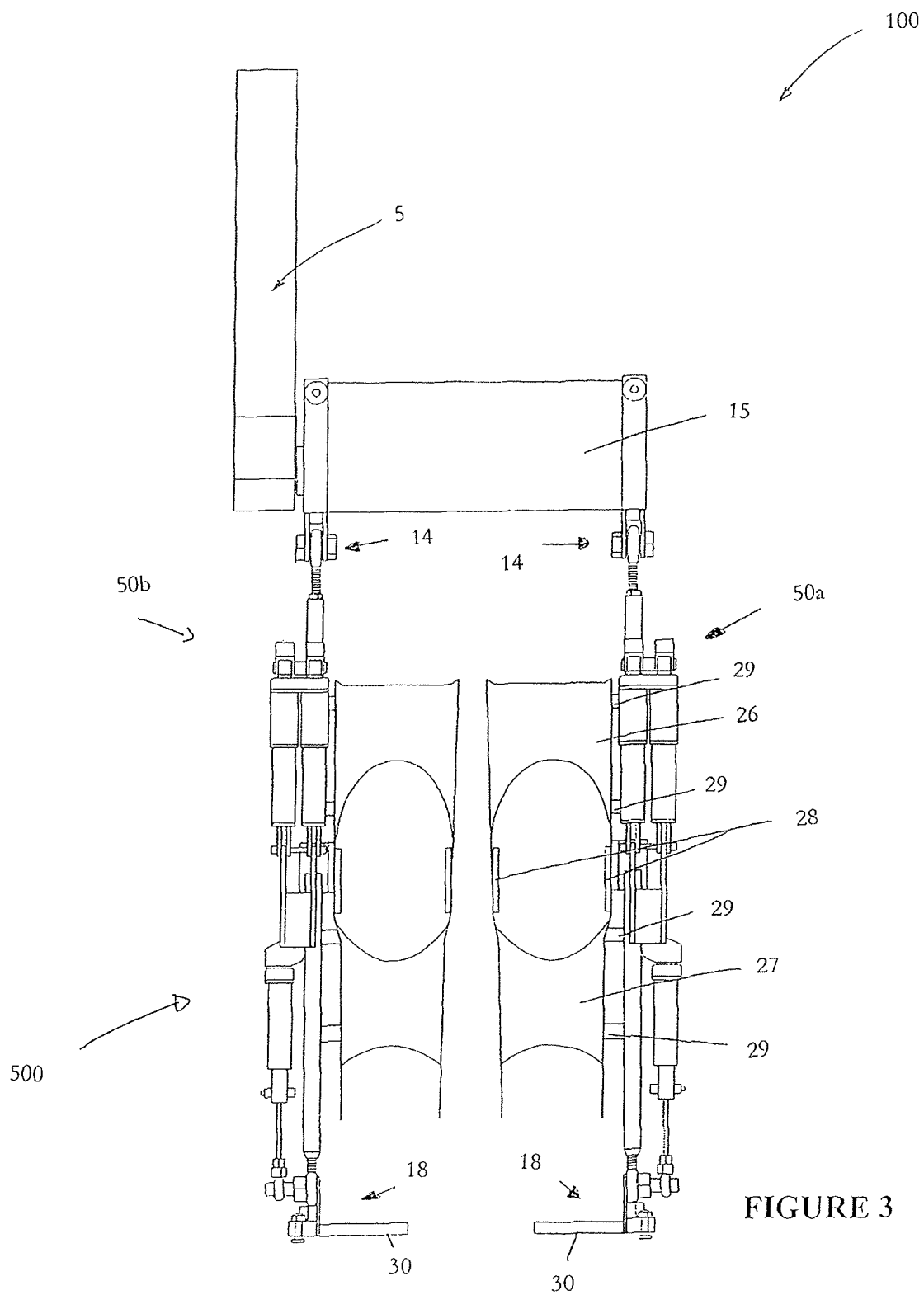
FIG. 3 is a front view of the exoskeleton and orthotics shown in FIG. 1.

The orthotics are preferably engaged and/or capable of being releasably engaged to the exoskeleton. With reference to FIG. 3, the orthotics may include an upper leg orthotic 26 and a lower leg orthotic 27. These may be directly joined to each or indirectly joined to each other by the exoskeleton. For example with reference to FIG. 3, the upper leg orthotic 26 and lower leg orthotic 27 may be joined at the joints 28. The orthotics are engageable to the exoskeleton 500 via connectors 29.

The connectors 29 rigidly hold the orthotics to the exoskeleton. The connectors 29 are of a shape and configuration so that a correct alignment of the upper and lower leg of the person is achieved once engaged to the exoskeleton. The connectors 29 may be of a dove tail configuration or snap lock configuration or other. The connectors 29 may facilitate a releasable engagement of the orthotics to the exoskeleton 500. This can be beneficial to a user 600 who normally wears orthotics. This allows for such a person to more rapidly associate themselves with the exoskeleton 500. It also allows for such a person to associate with the exoskeleton 500 in a comfortable manner because the orthotics 4 are already engaged to the person in an appropriate location.

The control of the walker is achieved by the control system which is configurable for controlling movement of the main hip actuators, secondary hip actuators, knee actuators, main foot actuators, and secondary foot actuators. A power source is configurable for providing power to the actuators 16, 13, 19, 38, 39.

Controlled movement of the actuators can cause movement of the exoskeleton 500 relative to the ground on which the walker is positioned. When controlled to actuate the actuators in the correct sequence, a walking gait like motion can be achieved by the exoskeleton. Further, when a mobility impaired disabled user 600 is secured to the walker, the user 600 is caused to move their joints and muscles through the motions of walking, thereby assisting in the prevention of deterioration of a user's 600 physiology.

The walker may be controlled by the user by way of a joystick 2 and keypad 3 normally positioned at waist height. The keypad 3 and joystick 2 may be supported by an arm 5. This may be able to pivot to move between at least one operational position (eg in use extending horizontally or pointing down vertically) and a retired position (eg extending vertically)

Figure 2:
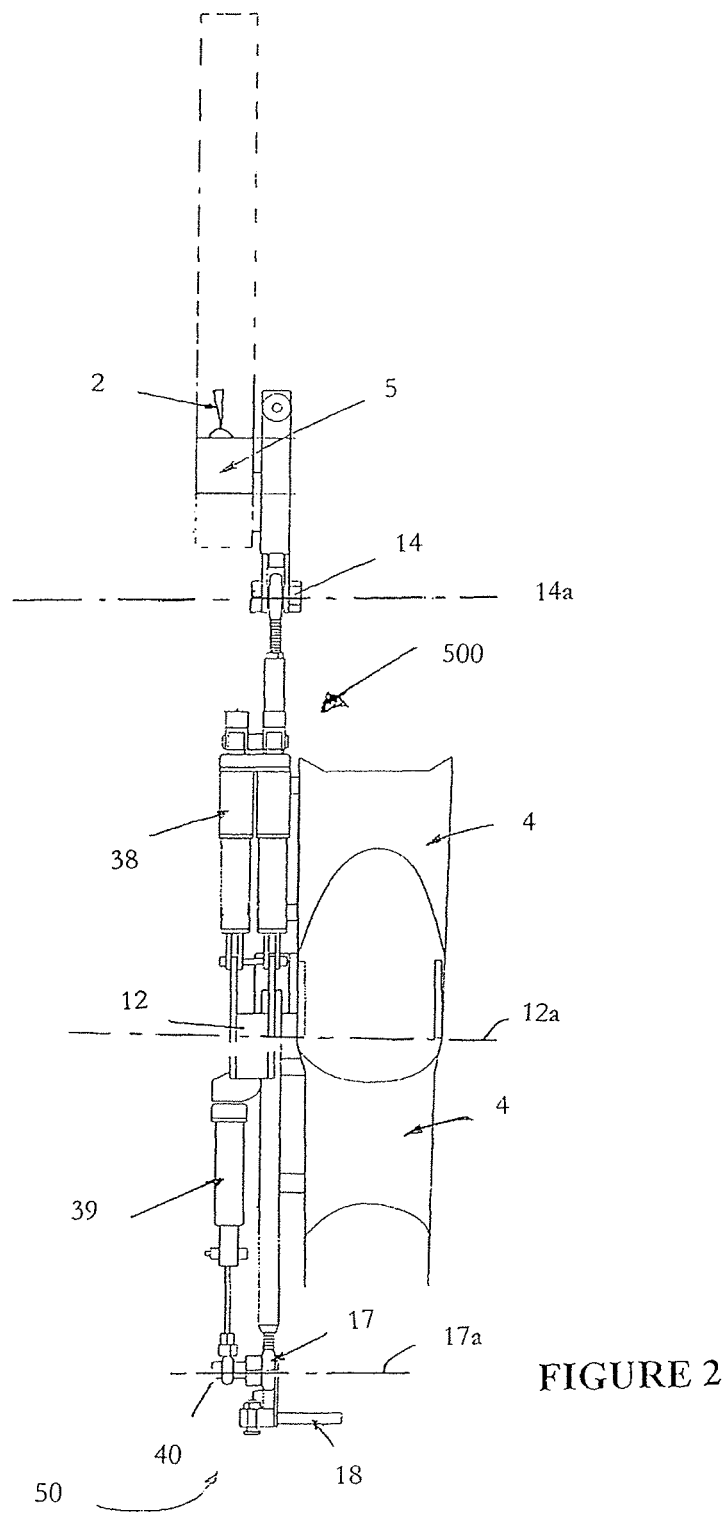
FIG. 2 is a cutaway front view of part of the exoskeleton and orthotics that is shown in FIG. 1.

More detail will now be described with reference to FIGS. 1-3. The exoskeleton 500 includes an upper leg structural member 10 and a lower leg structural member 11. These are connected by a knee joint 12 that defines a pivot axis 12A to allow the upper leg member 10 and lower leg structural member 11 to pivot relative to each other. The pivot axis 12A ensures the upper leg member and lower leg member can rotate relative to each other but only about one pivot axis. Alternatively a polycentric knee joint may be used.

Movement about the knee axis 12A of the upper leg member and lower leg member can be actuated by the knee actuator 13. The knee actuator 13 extends between parts of the upper leg member and lower leg member for the purposes of actuating relative rotational movement between the upper leg member 10 and lower leg structural member 11.

Figure 30:
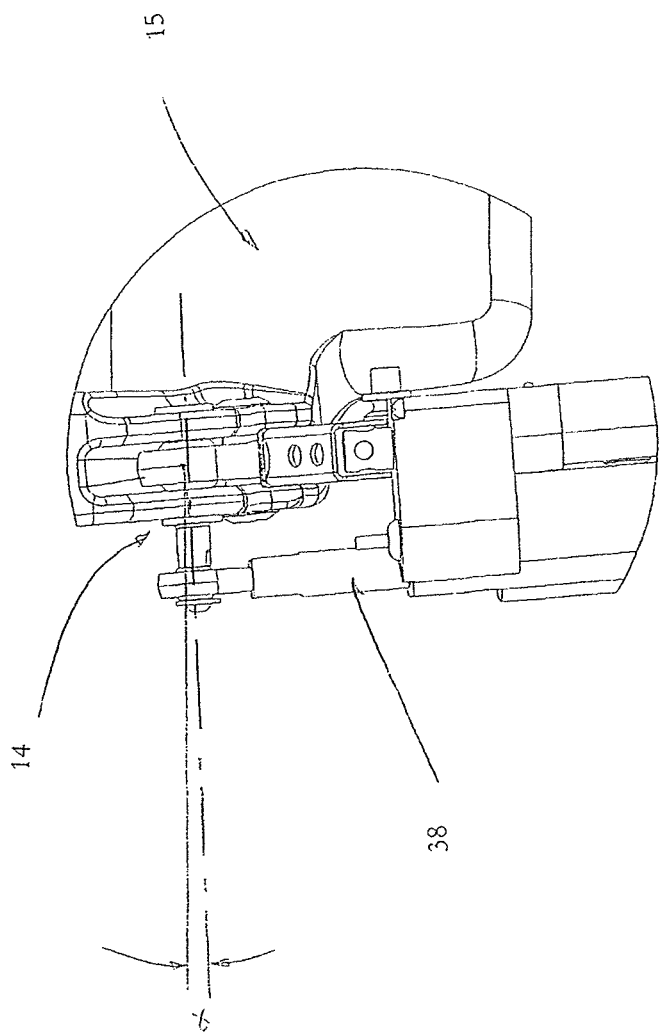
FIG. 30 shows a rear view of a region near the hip joint of FIG. 26.
Figure 31:
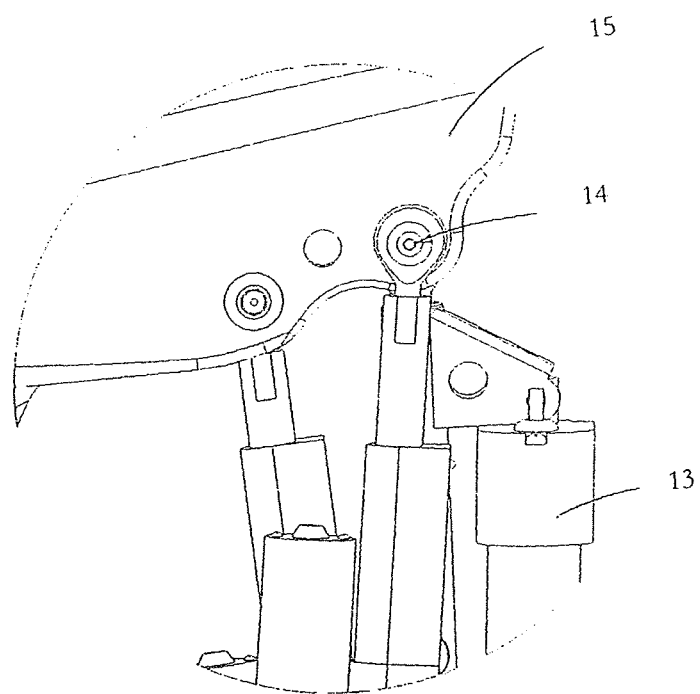
FIG. 31 shows a side view of a region near the hip joint of FIG. 26.
Figure 33:
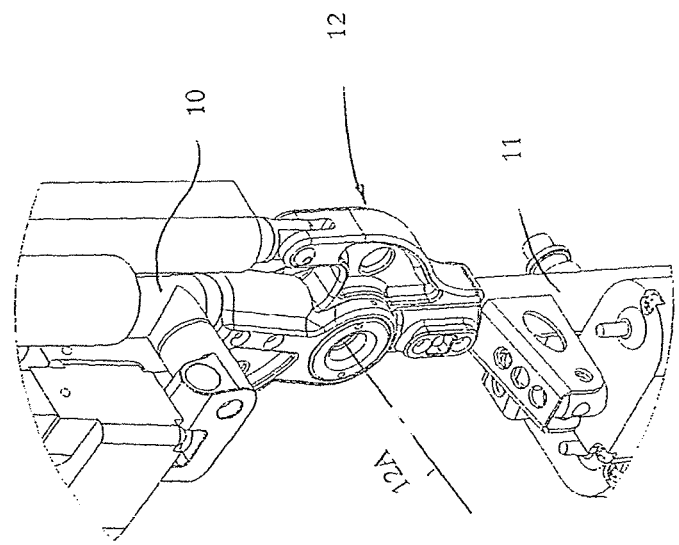
FIG. 33 shows a perspective front view of a knee joint of FIG. 26.
Figure 32:
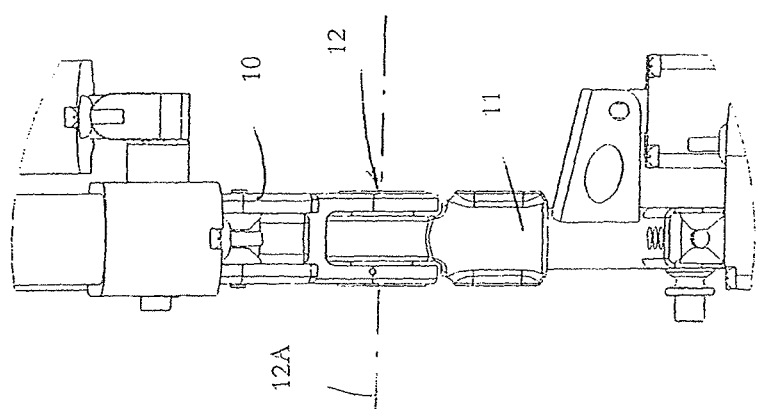
FIG. 32 shows a rear view of a region near the knee joint of FIG. 26.
Figure 34:
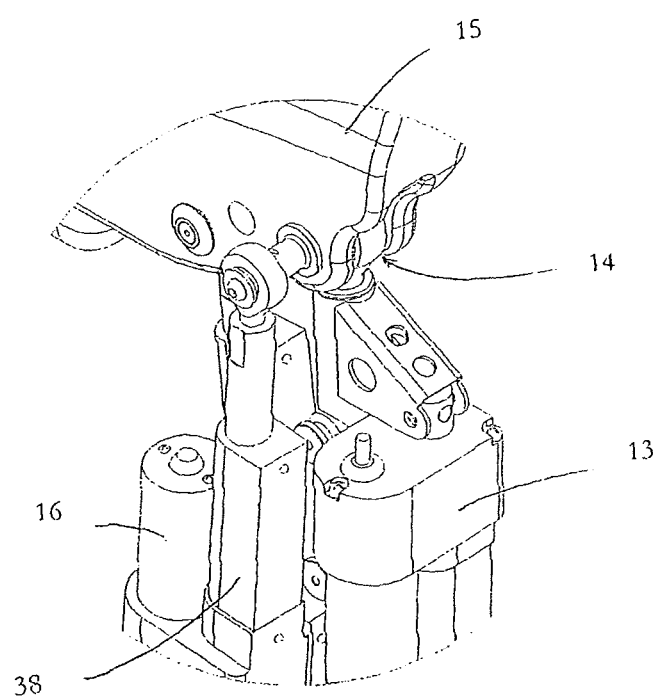
FIG. 34 shows a perspective front view of a region near the hip joint of FIG. 26.
Figure 35:
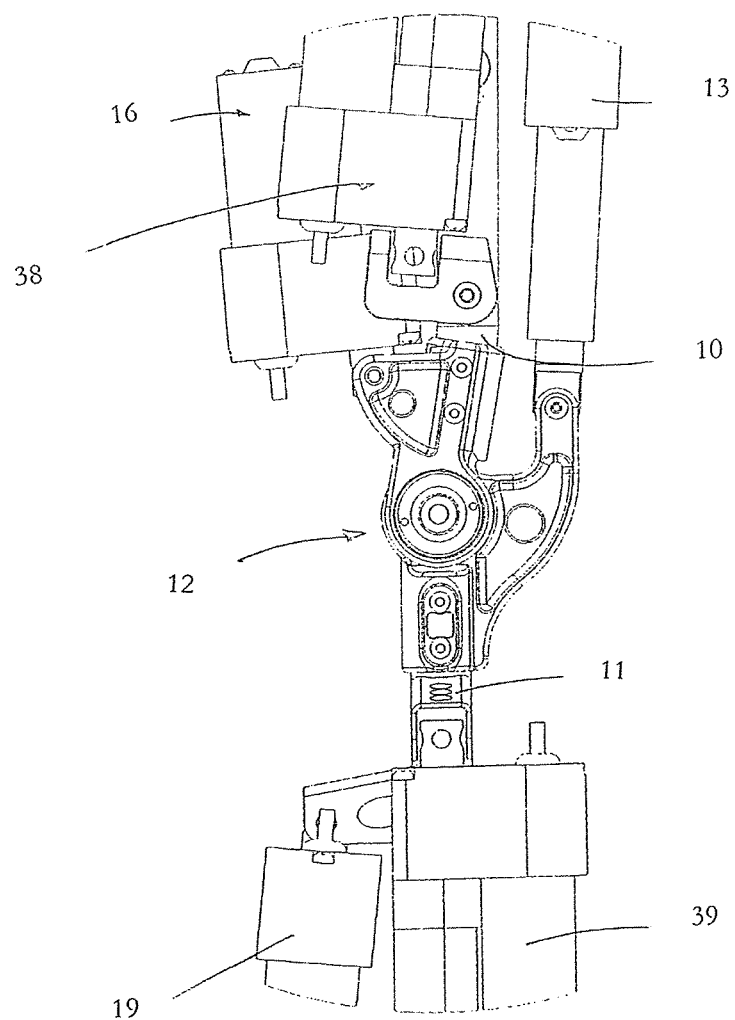
FIG. 35 shows a side view of a region near the knee joint of FIG. 26.
Figure 36:
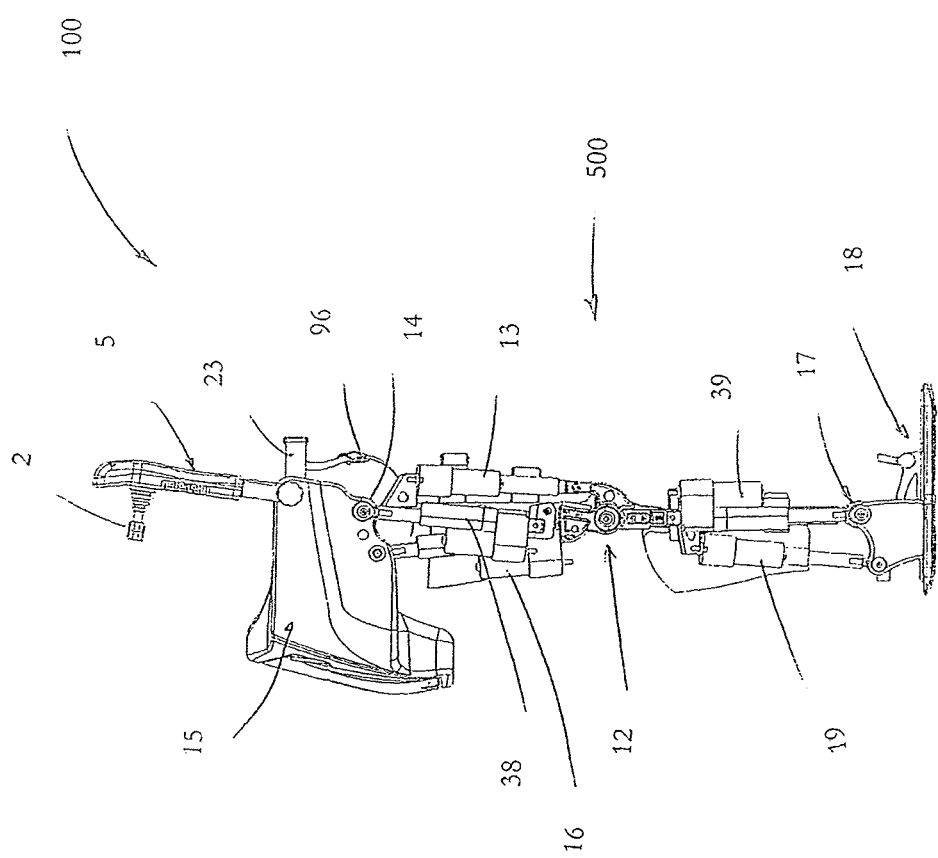
FIG. 36 shows a side view of a third embodiment of a walker in a standing position without covers on, FIG. 37 shows a side view of a third embodiment of a walker in a stepping position without covers on, FIG. 38 shows a side view of a third embodiment of a walker in a stepping position with covers on, FIG. 39 shows a front perspective view of a third embodiment of a walker in a sitting position without covers on, FIG. 40 shows a front view of a third embodiment of a walker in a sitting position without covers on, FIG. 41 shows a front perspective view of a region near the foot joint of a walker.
Figure 37:
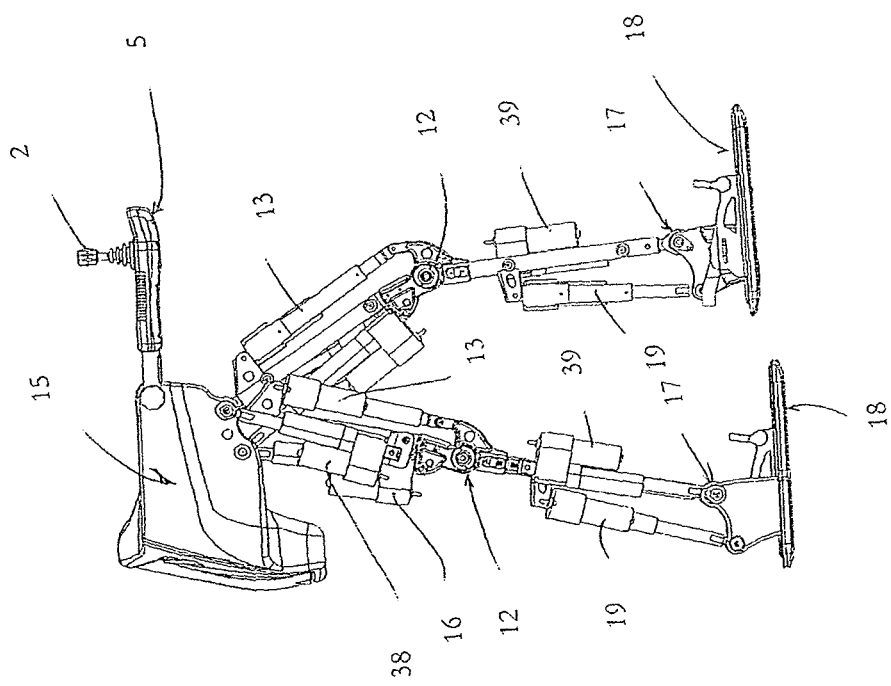
Figure 38:
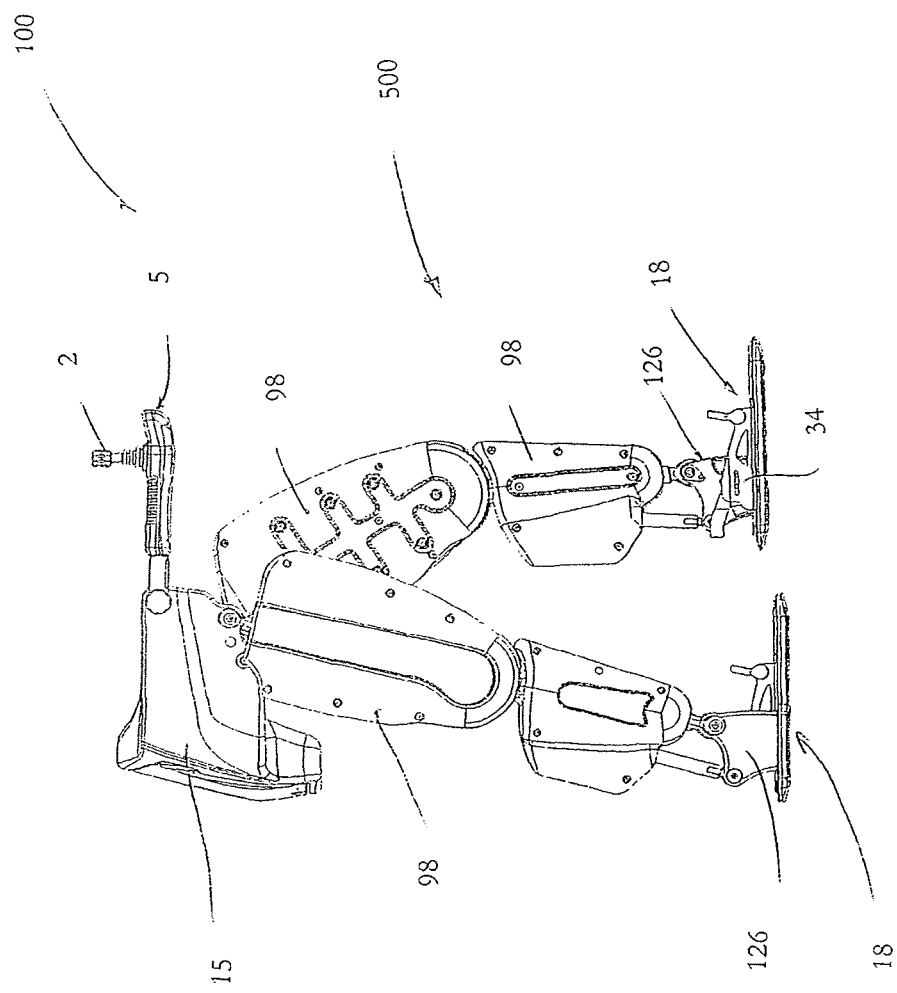
Figure 43:
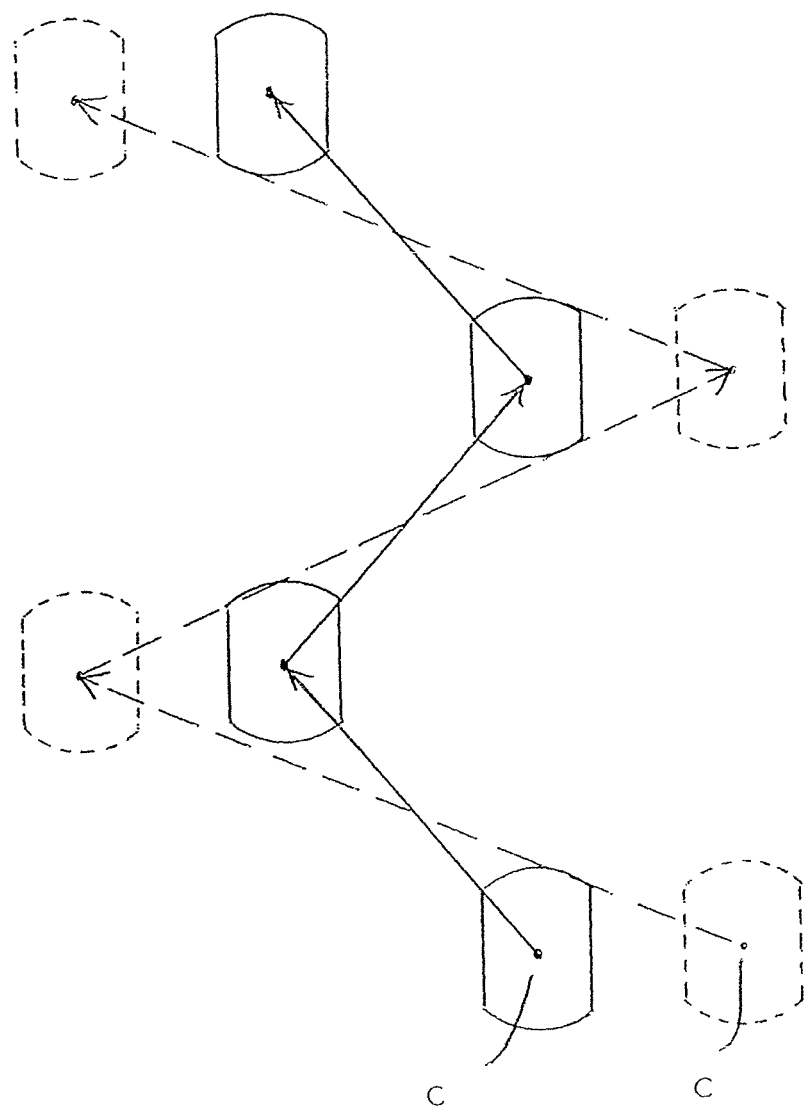
FIG. 43 shows a schematic diagram illustrating the movement of centre of mass of the walker and user between steps during a walking movement.
Figure 44:
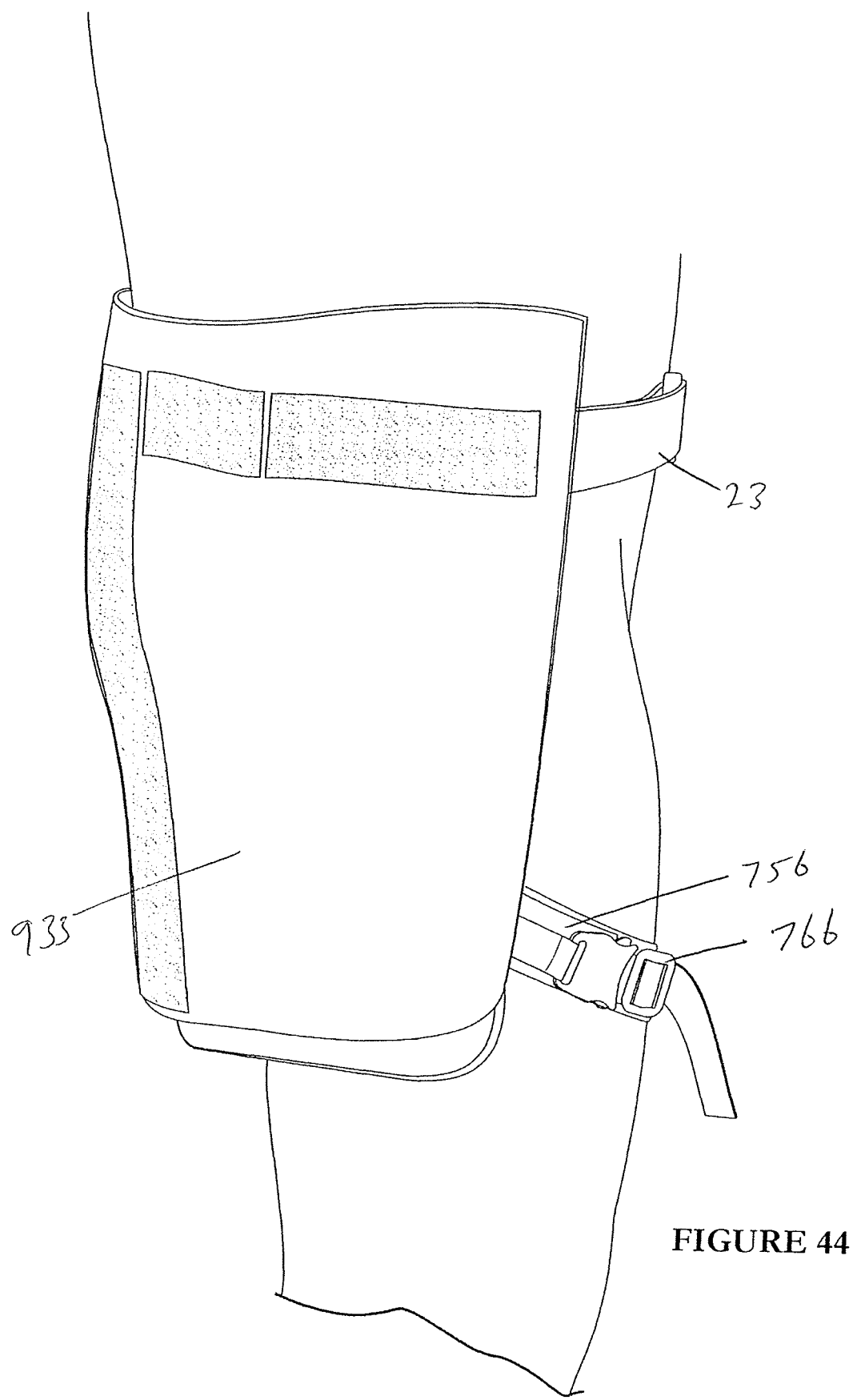
FIG. 44 shows a side view of the user support harness and associated spacer.

The knee joint 12 is preferably located at a distal first end 10b of the upper leg member 10. At a first end 10a of the upper leg member 10 is a hip joint 14 that pivotally engages the upper leg member 10 with the pelvic support member 15. The hip joint 14 defines a hip axis 14A that in use is located relative to the user 600 at or approximate to the natural axis of hip rotation towards and away from the coronal plane. In a preferred embodiment, each hip joint 14 is configured relative to the pelvic support member 15 with its axis of rotation 14A extending downwardly in a lateral direction (i.e. substantially parallel to the coronal plane) at an angle of between zero and ten degrees, and more preferably at about four degrees to the transverse plane. This inclination of the axis of rotation 14A mimics as a close approximation a human beings upper leg alignment and is illustrated as angle α in FIG. 30. The inclination means that the foot members of the walker 100 are closer together, which allows for more natural transfer of the centre of mass (generally located about the middle of the pelvis) to a point within the support area provided by the foot members 18 during when the walker 100 is controlled in to move through a walking motion. This is further illustrated in FIG. 43, showing how the movement of the combined centre of mass (illustrated as point C) of the walker 100 and the user moves in a reduced side to side movement between the individual steps in a walking movement, compared to a walker not having such an inclination of the axis of rotation of the hip joint (shown in broken lines).

The hip joint 14 allows for a relative rotation between the upper leg member 10 and the pelvic support member 15. Such rotation is preferably primarily about an axis that is parallel to the knee axis 12A. However the hip joint 14 may also allow for a rotation of the upper leg member 10 relative the pelvic support member 15 in an abduction and adduction manner. This multi axis pivoting capability can be facilitated by the use of a rose joint to define the hip joint 14. It is envisaged that the hip joint 14 (in the form of a rose joint) may be limited in its movement by a pair of horizontally aligned plastic, and preferably acetyl, bushes (not shown) disposed on either side of the rose joint. A vertically aligned flange (not shown) connected to the upper leg structural member 10 will be prevented from pivotal movement in a horizontal plane in this way, at least partially preventing pivoting movement of the upper leg structural member 10 about its longitudinal axis.

Rotation of the pelvic support member 15 relative the upper leg member 10 about an axis parallel to the knee axis 12A, at the hip joint 14 can be achieved by the use of the main hip actuator 16.

Disposed at a second distal end 1lb (the end away from the knee joint) of the lower leg structural member 11, is a foot member 18. The foot member 18 is capable to rotating relative the lower leg structural member 11 by virtue of the foot joint 17. The foot joint 17 preferably defines a pivot axis 17a that extends parallel with the knee axis 12A. Pivotal movement of foot member 18 about the foot joint 17 relative to the lower structural support member 11 towards and away from the coronal plane can be effected by the foot actuator 19.

The foot joint 17 may, like the hip joint, be a rose joint to facilitate its multi-axis pivoting capability. The foot joint 17 can allow for the foot member 18 to have multiple degrees of rotational movement relative the lower leg structural member 11. In a preferred embodiment, each foot joint 17 is configured with its axis of rotation 17A extending downwardly in a lateral direction at an angle of between zero and 6 degrees, and more preferably at about four degrees.

A secondary foot actuator 39 may be provided, and coupled to the foot member 18 to control a rotational movement of the foot member in a direction substantially transverse to the direction in which the main foot actuator 19 can control rotational movement towards and away from the sagittal plane. The secondary foot actuator 39 may be engaged to an axle or lever arm 40 of the foot member 18 to facilitate this pivoting movement.

Figure 5:
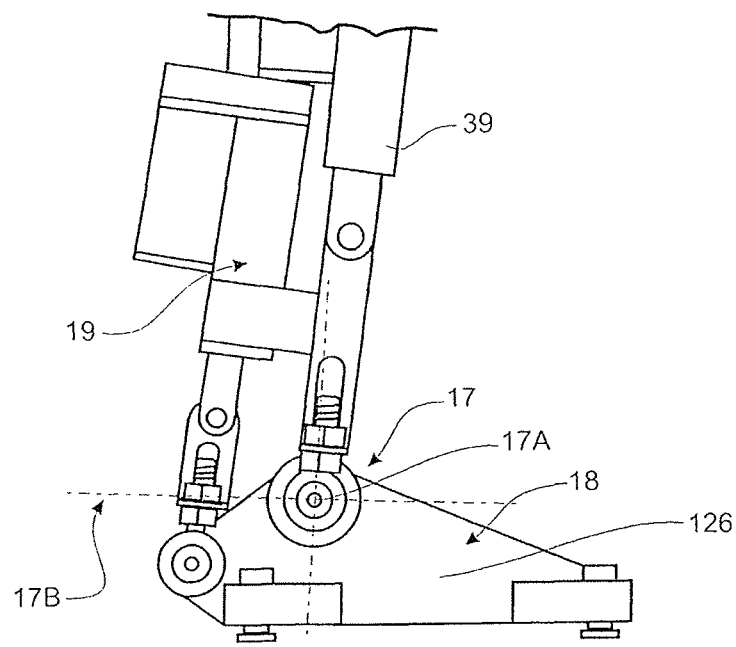
FIG. 5 is a cutaway side view of part of the exoskeleton of FIG. 1 in the region of the foot member.
Figure 6:
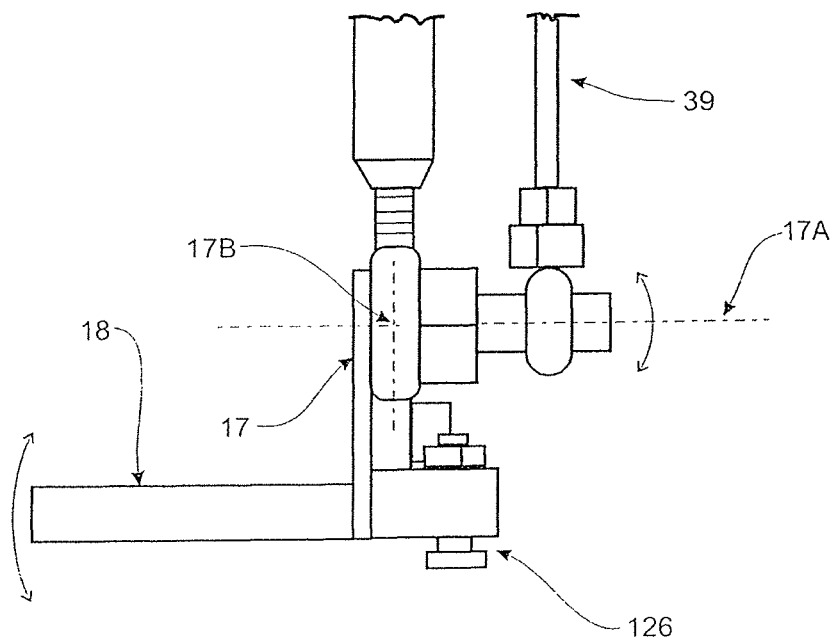
FIG. 6 is a rear view of FIG. 5.

With reference to FIGS. 5-6, in FIG. 5 there is shown a close up view of the foot member 18, foot joint 17 and lower leg structural member 11 of the device, wherein it can be seen that a secondary axis 17b is provided about which the foot member 18 can rotate as a result of operation of the secondary actuator 39.

Figure 7:
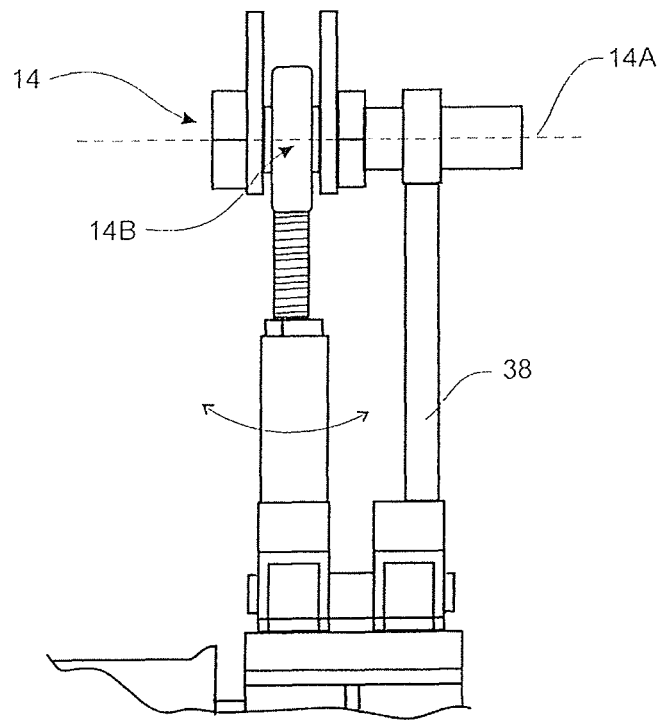
FIG. 7 is a cutaway front view of part of an exoskeleton including a secondary hip actuator in the region of the hip joint.
Figure 8:
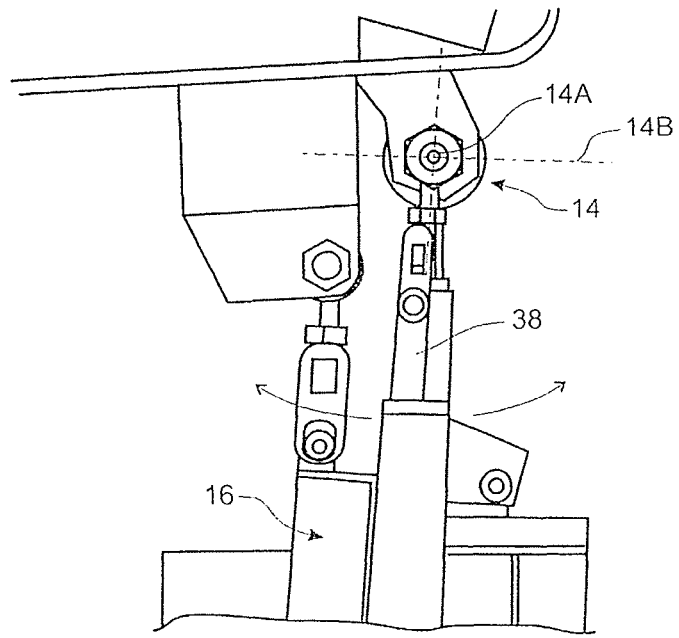
FIG. 8 is the side view of FIG. 7.
Figure 8A:
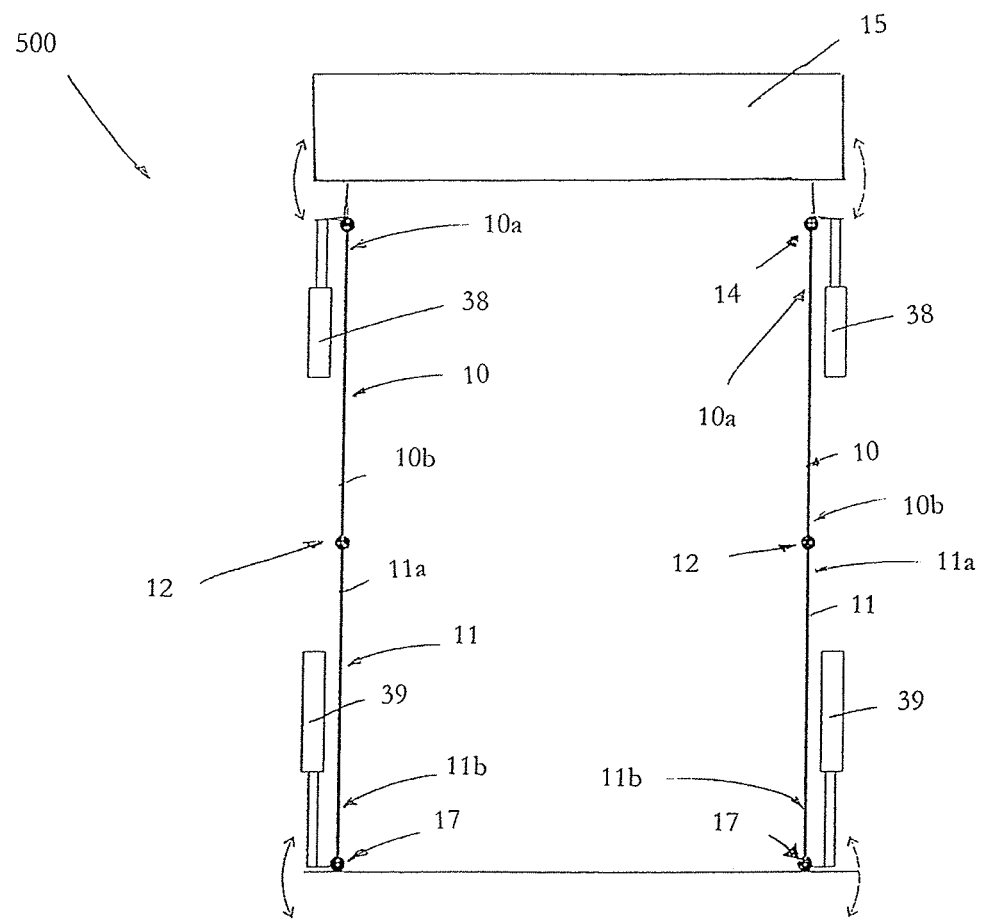
FIG. 8a shows a schematic layout of the lateral movement actuators of the exoskeleton seen from the front.
Figure 12:
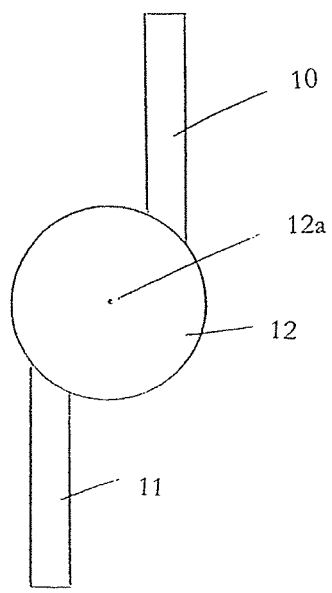
FIG. 12 shows a side view of the knee joint in schematic form showing the offset of the knee joint.

FIGS. 7-8, show a primary axis of rotation that is about axis 14a and a secondary axis defined by axis 14b, movement about which can be controlled by the secondary hip actuator 38.

To allow for the walker 100 to be fitted to a user to allow the user to operate the device in a safe manner, it is important to ensure that the spacing between hip joint 14, knee joint 12 and foot joint 17 is appropriate. Appropriate positioning should be where such joints are, as close as possible, aligned with the corresponding natural joints of a user.

The exoskeleton 500, when worn by a user will sit relative a user 600 in a position defined by a combination of factors. The user is preferably held to the exoskeleton by the use of orthotics 4 that are engaged to the exoskeleton. Adjustment of the position of the hip joint, knee joint and foot joint is achieved by virtue of adjustability in the effective length of the upper leg member 10 and the lower leg structural member 11. Such adjustment may be achieved by a turn buckle style adjustment means 20 that may be located at the second distal end of the lower leg structural member 11 and a turn buckle 21 at the first distal end of the upper leg member 10. The turn buckle 21 can allow for the distance between the hip joint 14 and knee joint 12 to be varied and the turn buckle 20 can allow for the distance between the knee joint and the foot joint 17 to be varied. In an alternate embodiment, the length adjustment may be accomplished by the insertion of lengthening inserts, which may be screwed into the upper and lower leg structural members 10, 11. It will be appreciated that adjustment features can be provided elsewhere and may also come in different forms such as in the form of a snap fit arrangement, bayonet type arrangement, telescopic or other means of setting the distance between the joints. This adjustment can allow for the one device to be used by different users that may be of differing body shape or size.

The walker is primarily designed for use by paraplegic users who are unable to exercise any control over their legs and feet. The walker provides stability to the user in a standing and walking gait by the features described herein that substitute the anatomical functions of the user that the user needs to stand and walk but that the user has lost control over. Such a mobility impaired disabled users needs to be fully supported as they are not able to stand by themselves. In this context, the walker offers full support to a mobility impaired disabled user for standing and during a walking gait. In addition an important aspect of the walker is its ability to support the mobility impaired disabled user in a position so that their own legs are weight bearing. This causes their bones to be subjected to stress. Typically, mobility impaired disabled user's leg and pelvic bones deteriorate over time. This is caused by the removal or leeching of minerals from their bones where their bones are not subjected to regular stress. In addition to the weakening of their bones, mobility impaired disabled users can suffer from downstream complications from this mineral removal, in that these minerals may build up in other parts of their bodies, for instance in, such as kidney stones or the like.

In subjecting a mobility impaired disabled user's bones to stress where they would otherwise not be, helps prevent deterioration of a user's bones, and subsequent complications where minerals removed from the user's bones builds up elsewhere in the user's system. Further, causing movement of the user's legs assists in stimulating blood flow through their system, which allows associated physiological benefits. The leg structures of the exoskeleton are able to be adjusted in length in order to tune the degree of stress that the users legs are places under. This length adjustability is important in order to ensure for example that a new user can receive a custom set walker for use that will have significant adverse effects on their body. Or in case a new user is changing in height and requires the walker to be re-tuned.

Figure 16:
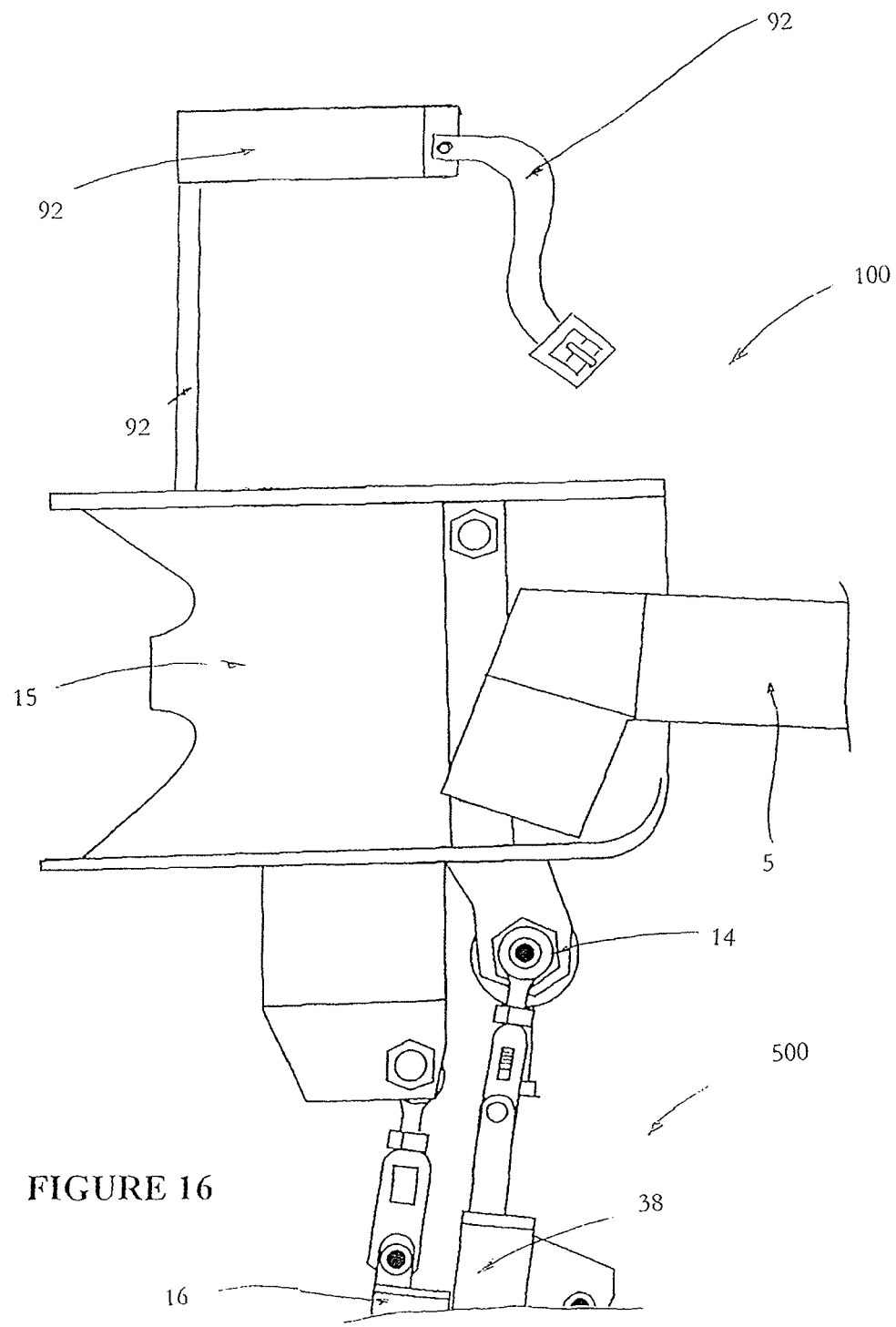
FIG. 16 shows a side view of an upper region of the exoskeleton including an upper body control extension for supporting upper body movement relative to the pelvic brace.
Figure 17:
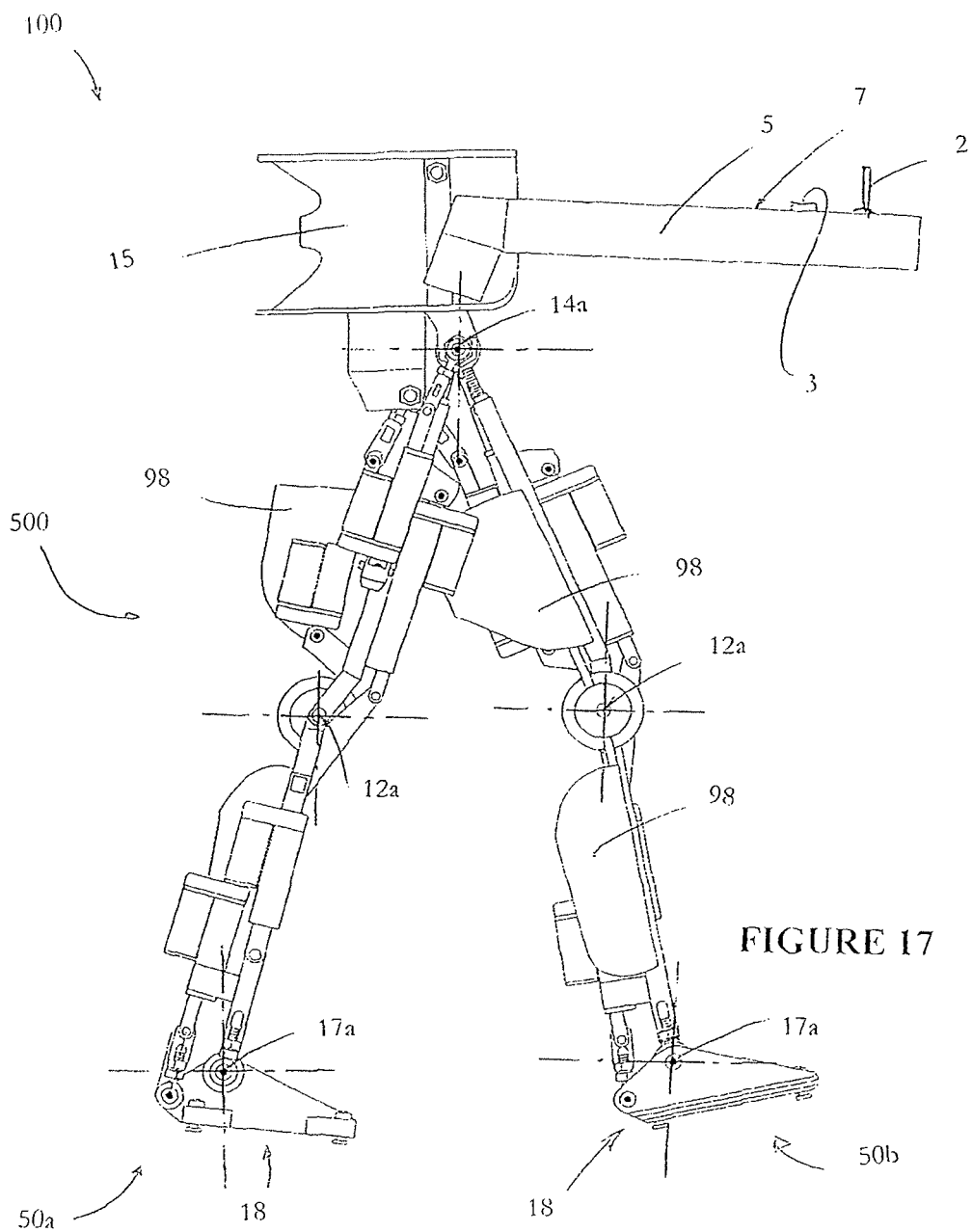
FIG. 17 shows a side view of a walker in a stepping forward position.
Figure 18:
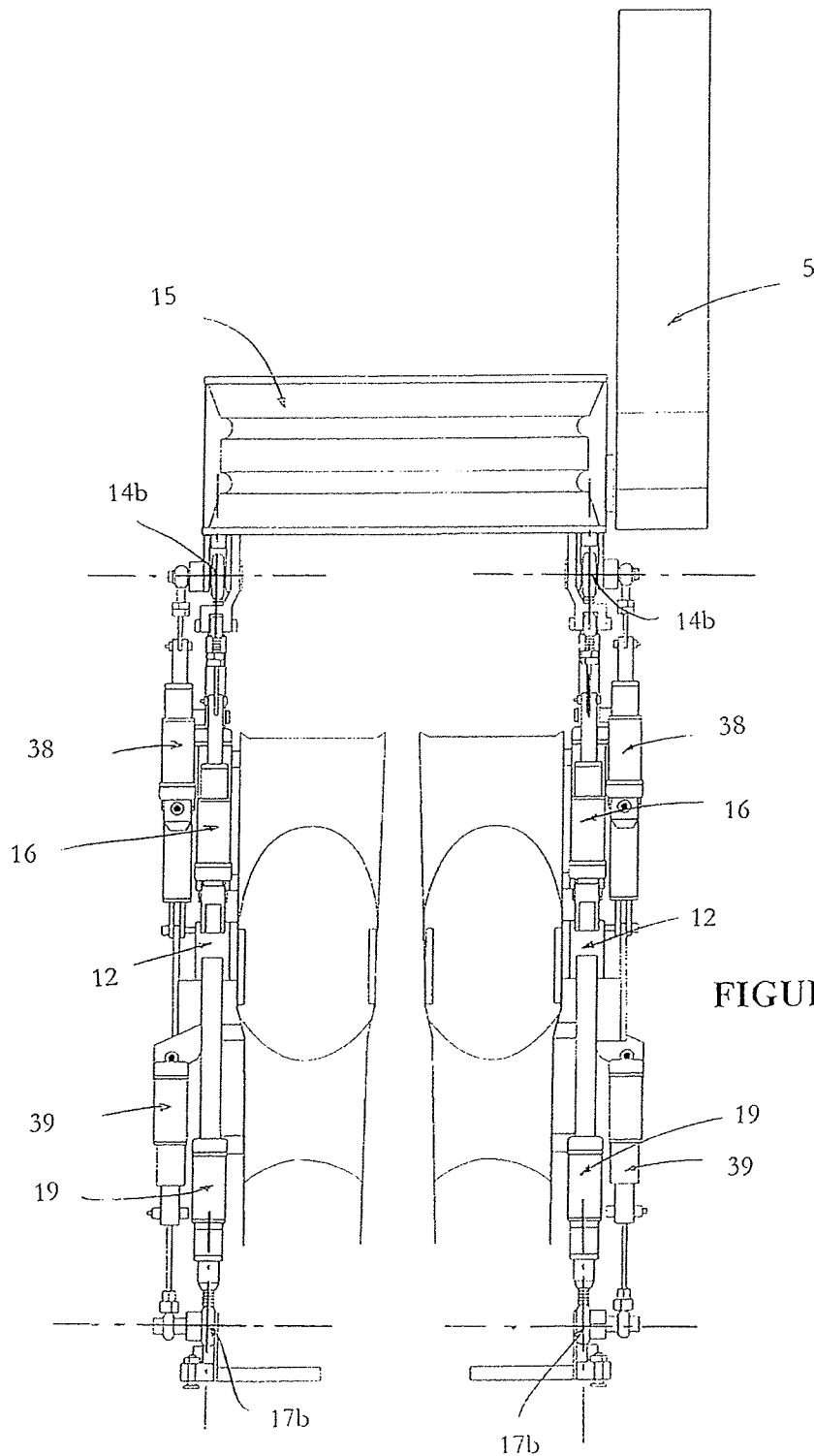
FIG. 18 shows a rear view of a walker including a secondary hip actuator.
Figure 19:
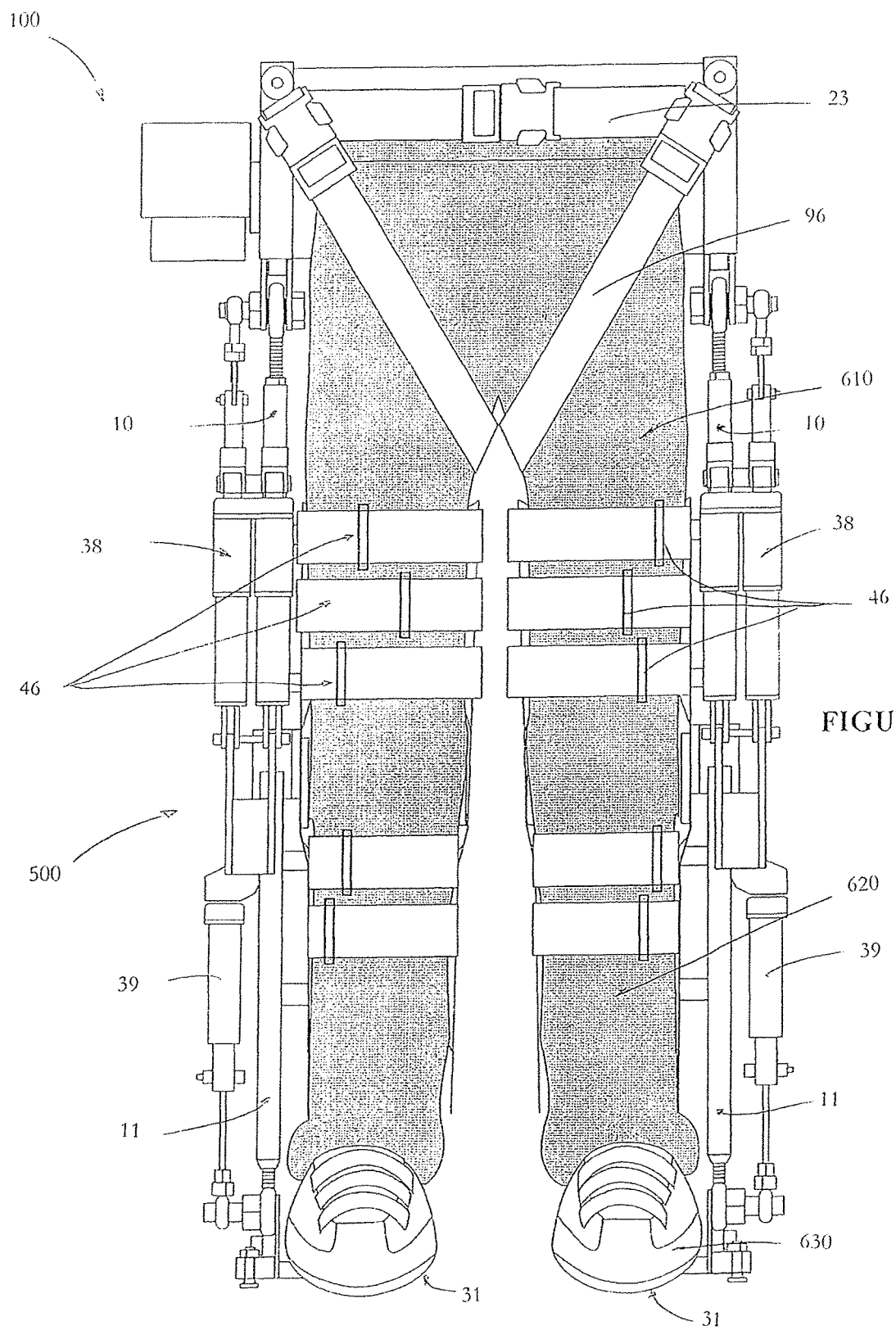
FIG. 19 shows a front view showing in more detail the bracing and support that is provided to secure the user by the exoskeleton.
Figure 20:
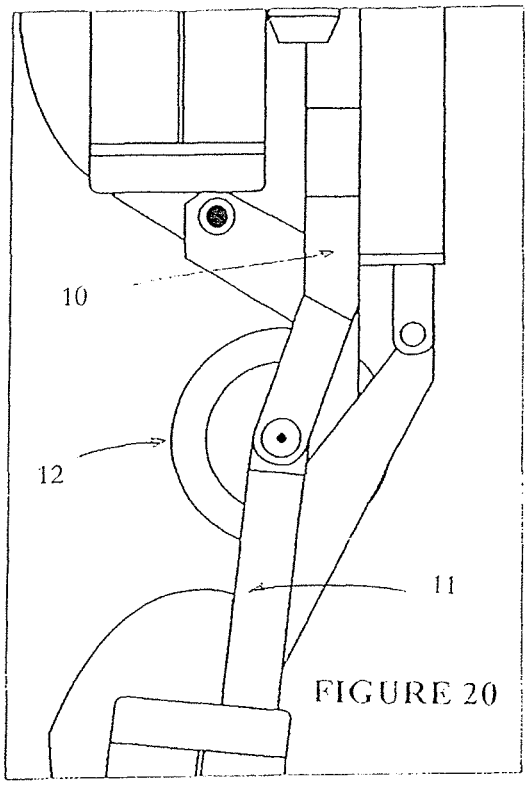
FIG. 20 shows a cutaway right side view of the knee region of the exoskeleton showing a knee pivot offset.
Figure 21:
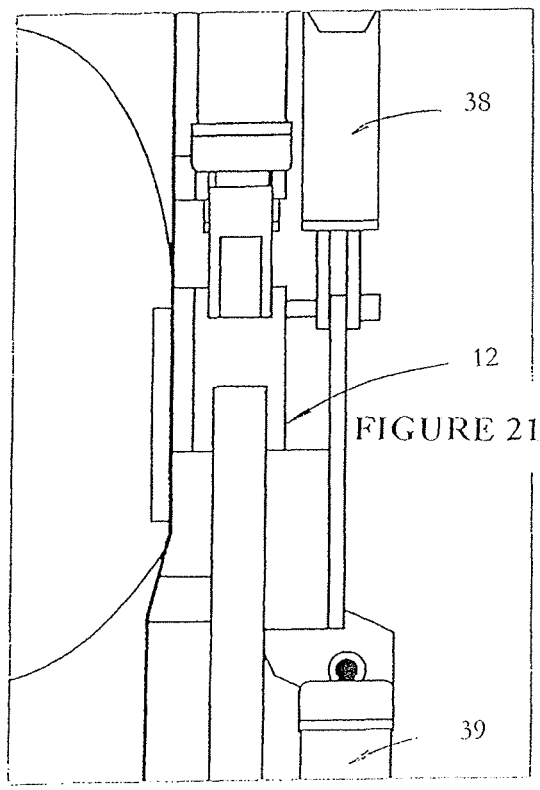
FIG. 21 shows a cutaway right rear view of the preferred knee pivot off set.
Figure 22:
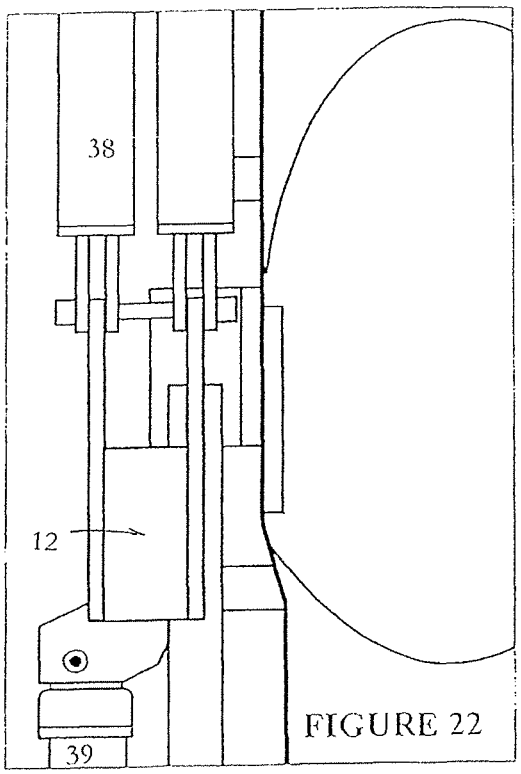
FIG. 22 shows a cutaway right front view of the knee pivot offset.
Figure 23:
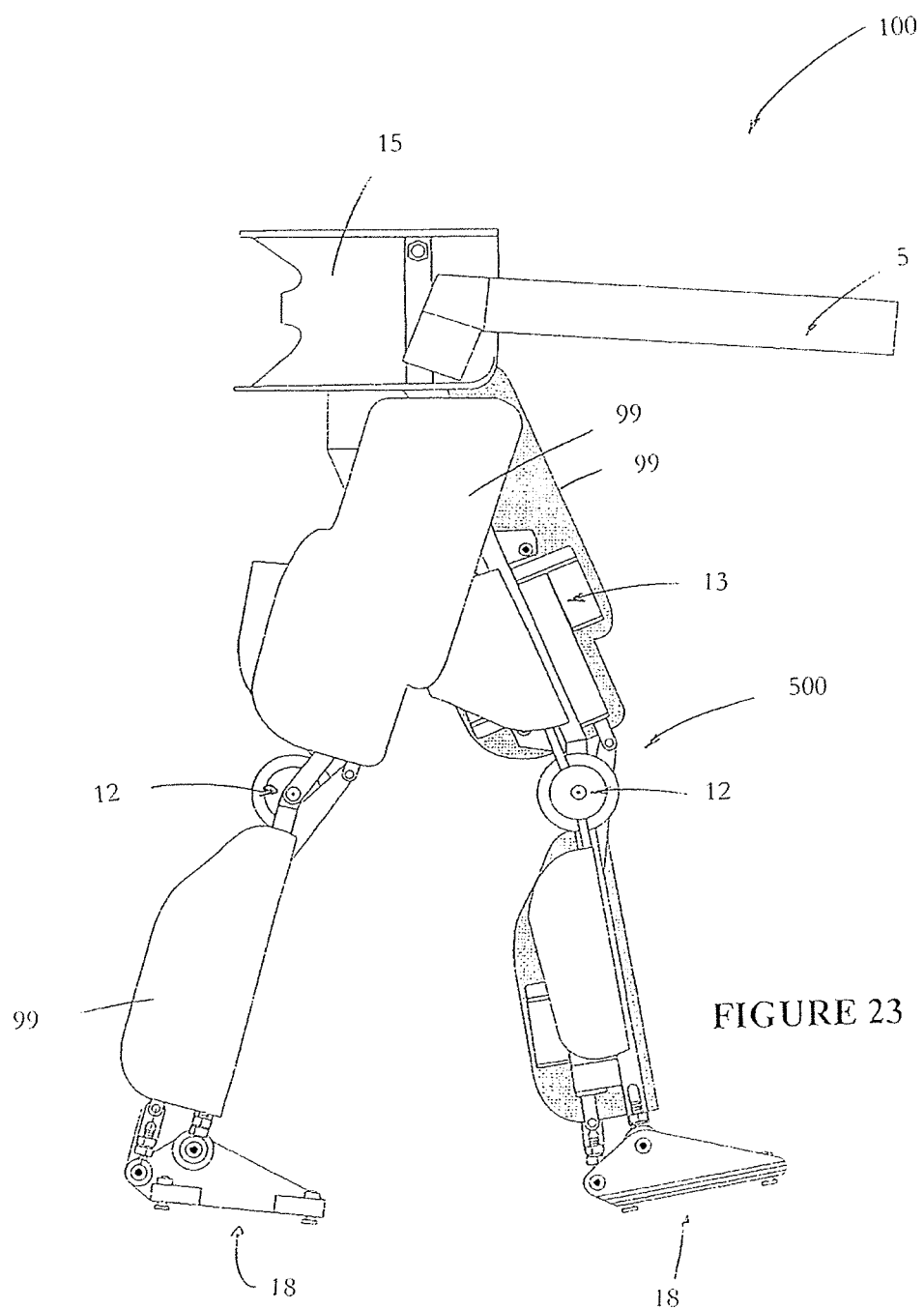
FIG. 23 shows a side view of a walker with covers on, FIG. 24 shows a rear view of a walker with covers on, FIG. 25 shows a front view of a walker with covers included and supporting the user.
Figure 24:
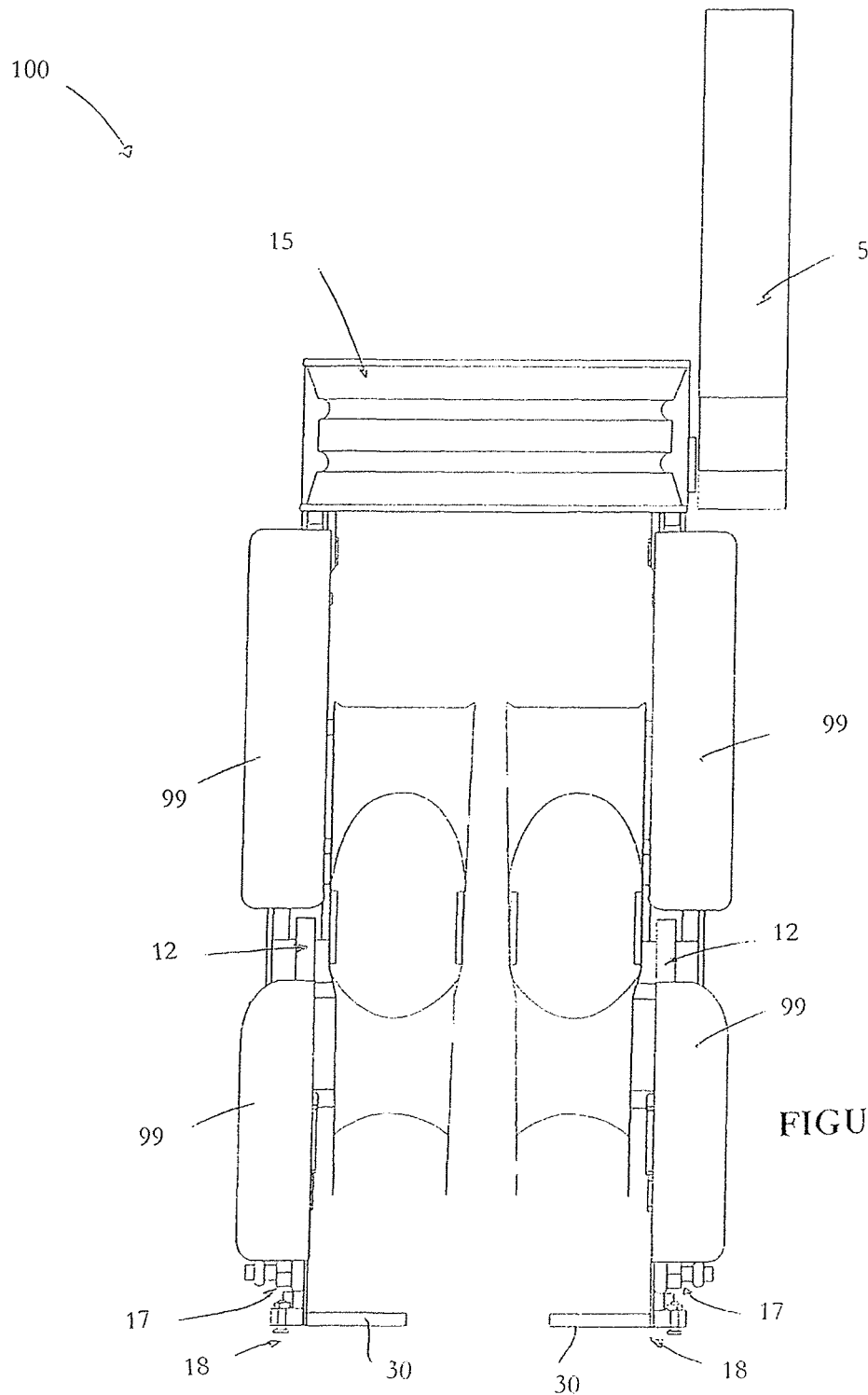
Figure 25:
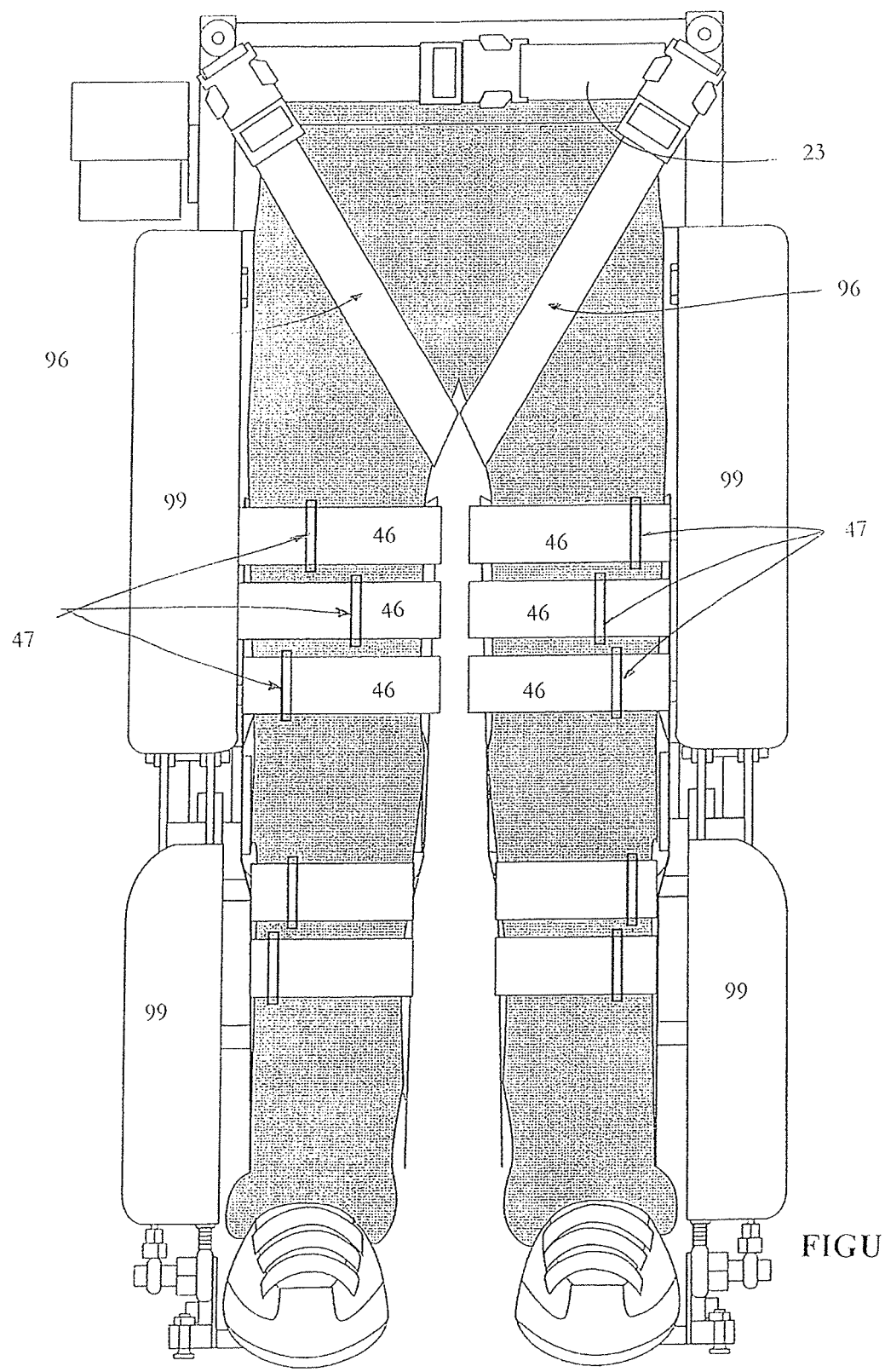
Figure 26:
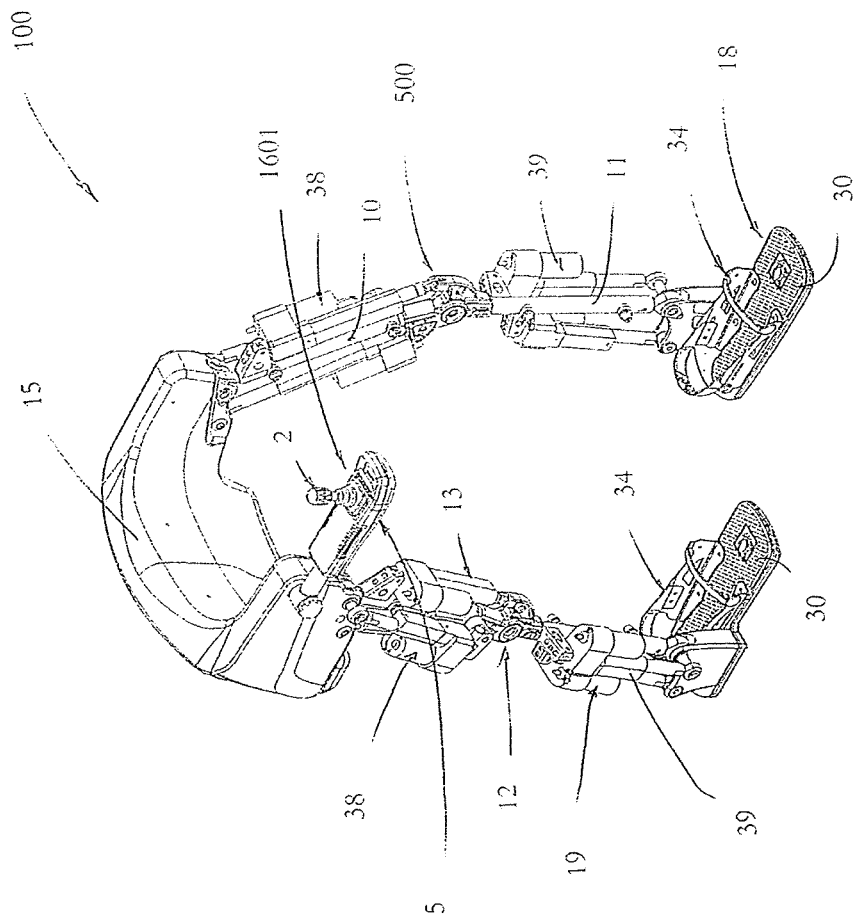
FIG. 26 shows a perspective front view of a third embodiment of a walker in a stepping position.
Figure 27:
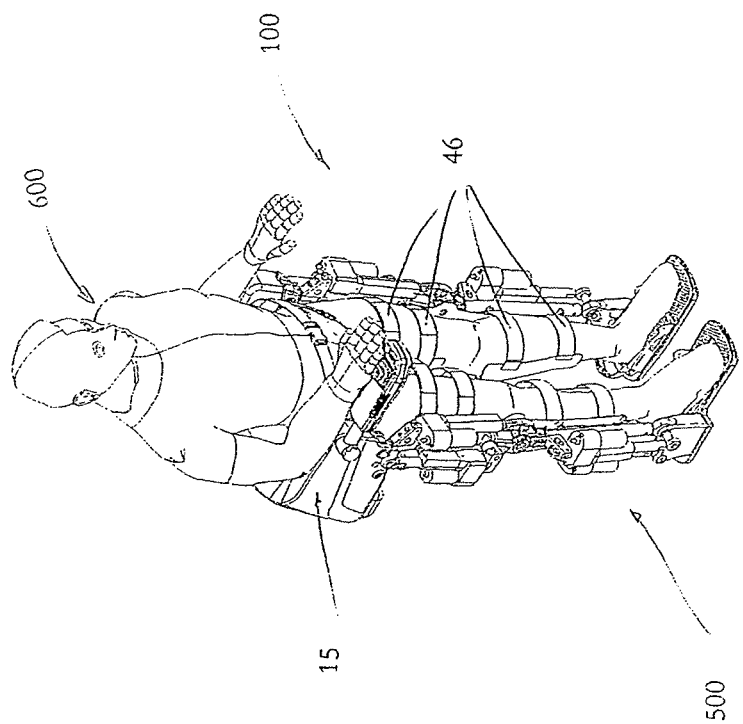
FIG. 27 shows a perspective front view of a third embodiment of a walker supporting a user in a standing position.
Figure 28:
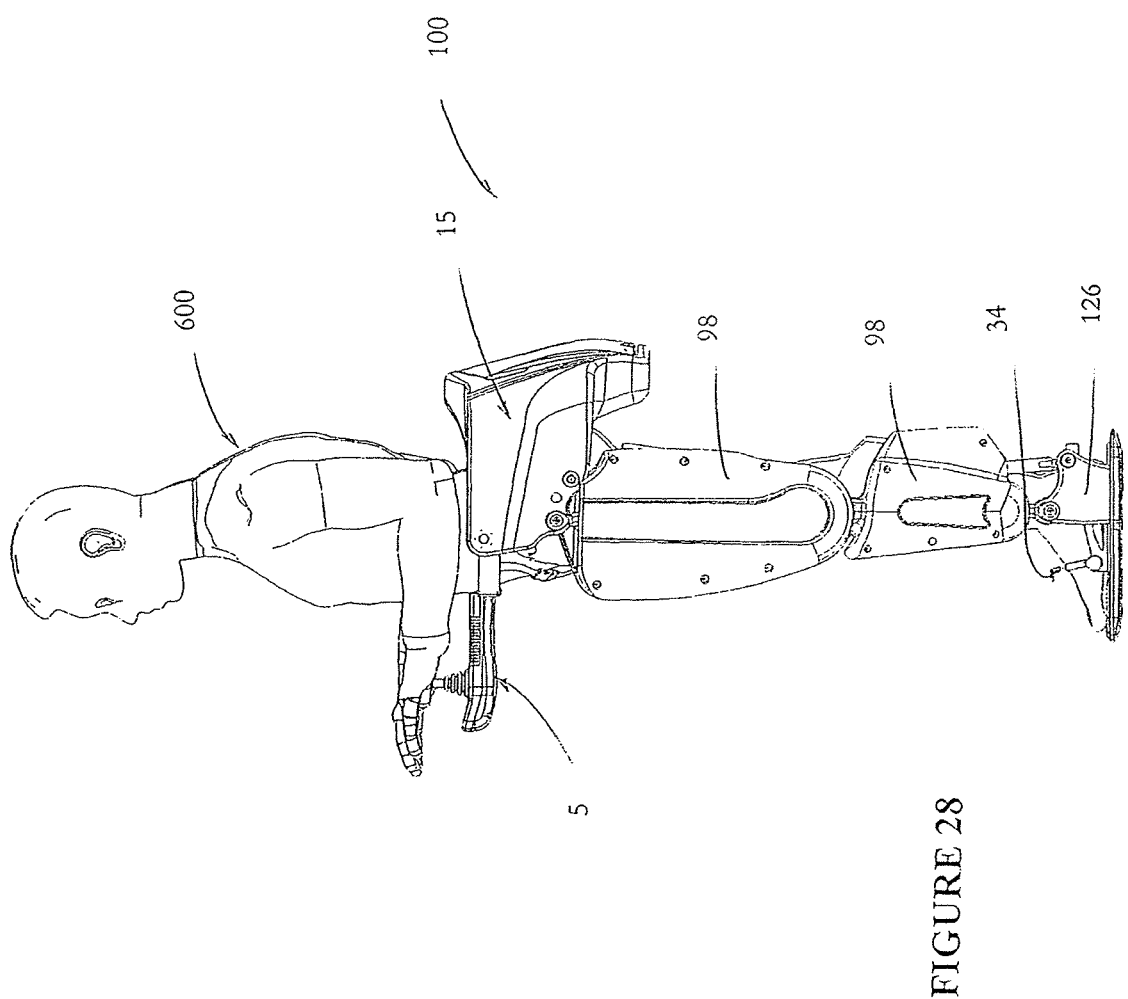
FIG. 28 shows a side view of a third embodiment of a walker supporting a user in a standing position.
Figure 29:
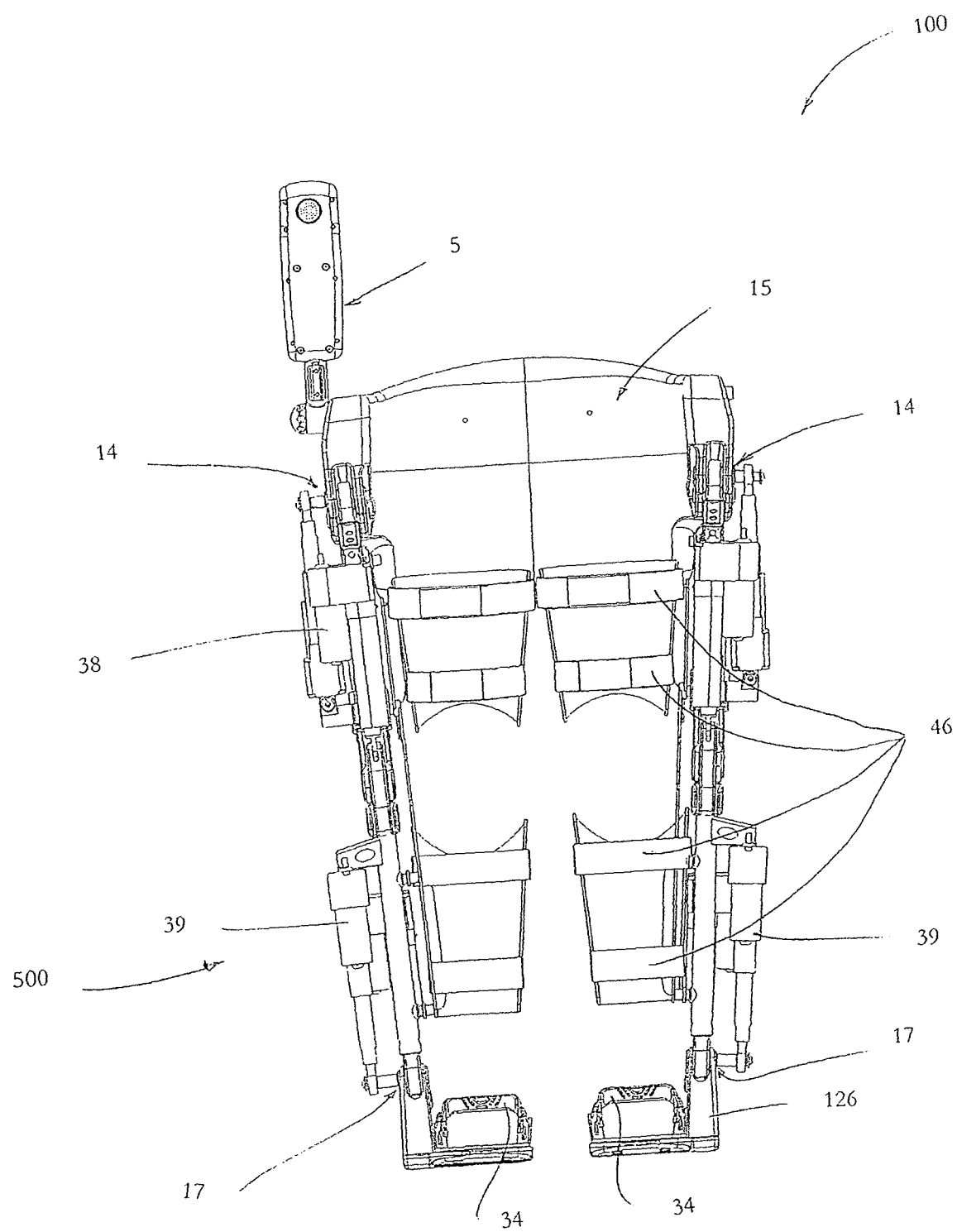
FIG. 29 shows a front view of a third embodiment of a walker.

The pelvic support member 15 holds part of the hip joints 14 thereby setting a fixed spacing of the hip joints 14 relative each other. The pelvic support member 15 is preferably a rigid member that can sit about part of the pelvis of a user. Preferably the pelvic support member 15 extends substantially about the posterior of the pelvis region of a user 600 and to the sides of the user. The pelvic support member 15 or an extension member that may be removably engaged thereto may also extend to offer support to the lower torso or waist of the user. With reference to FIG. 16 there is shown an additional support making the device suitable for users with lack of upper body strength and or function. There may be provided one or more torso support in the form of a harnesses or upper body braces 92 that is attached to the pelvic support member 15. The upper body brace 92 can be provided for users 600 that have limited upper body control. This upper body brace 92 may include a frame or corset that is actuated to move the user's upper body 640 to help with their balance. In one embodiment (not shown), the torso support harness 92 can be connected to the pelvic support member.

Figure 4:
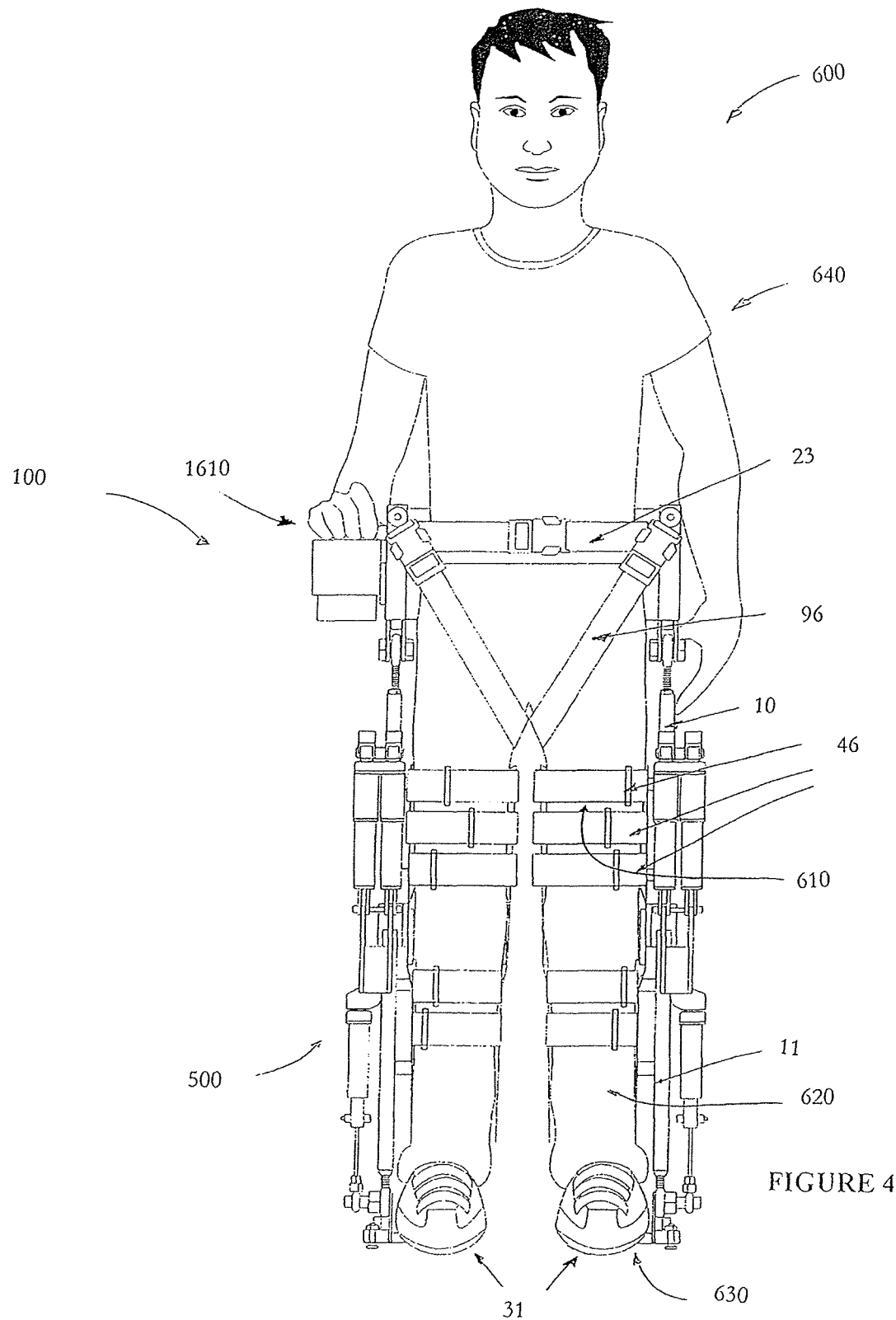
FIG. 4 is a front view of the walker of FIG. 1 supporting a user.

The user is supported at the pelvic support member 15 by a pelvic harness 96 which may include adjustable straps or webbing which extend about the legs of a user and are fastened and released as appropriate by the user. Such webbing may be adjustable in length. It may include the likes of a hook and loop fastening system such as Velcro® for facilitating easy entry and exit from the walker by the user. With reference to FIG. 4 it can be seen that the harness can include webbing 23. A user 600 can be strapped to the hip frame 15 by webbing 23 around their waist to ensure that the user remains firmly held to the hip frame 15. Further, a packing arrangement composed of a material such as wedge shaped foam or foamed plastic may be used to ensure a snug fit by the user in the hip frame 15. It is also envisaged that the packing arrangement 101 could be an inflatable thin walled pressure vessel (not shown).

Figure 39:
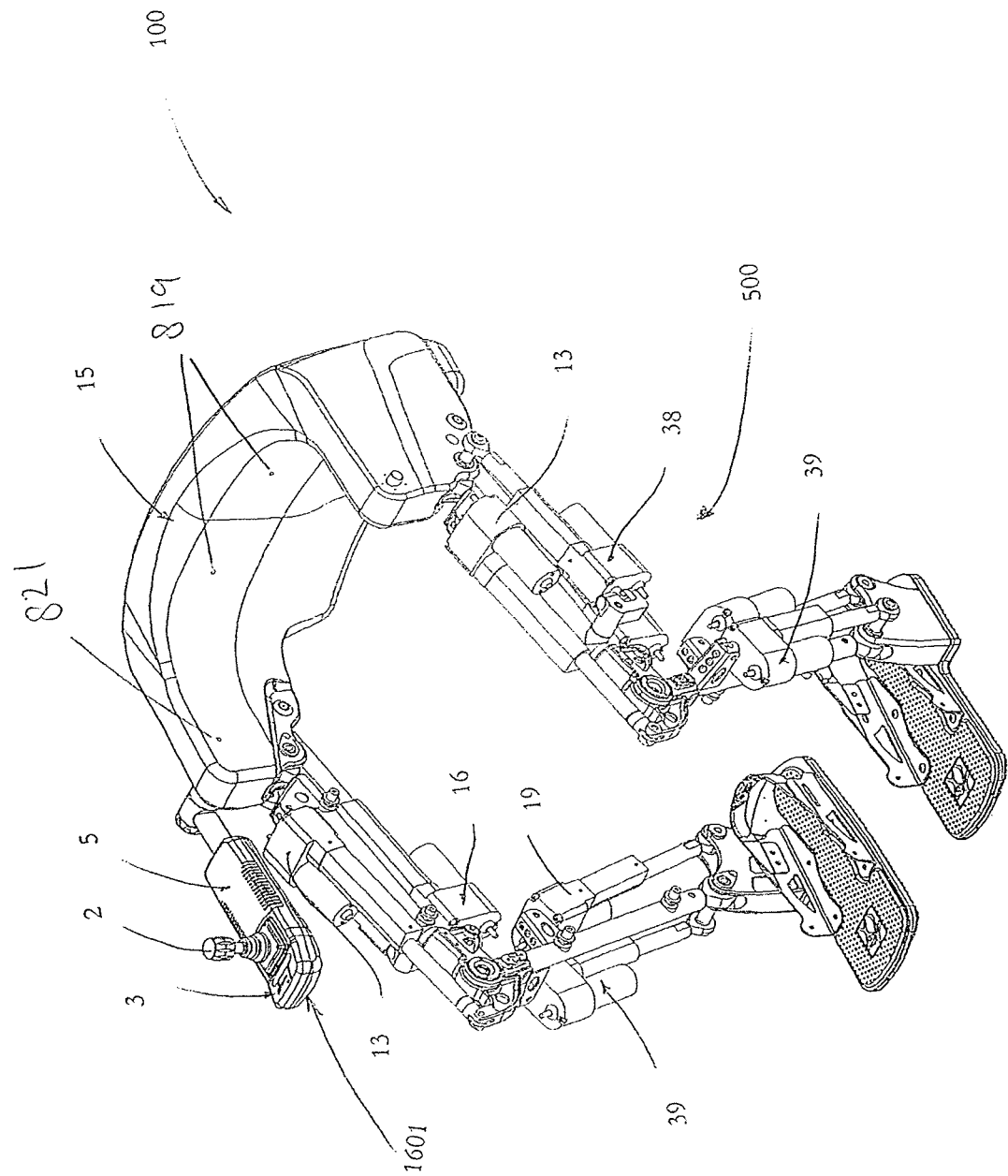
Figure 45:
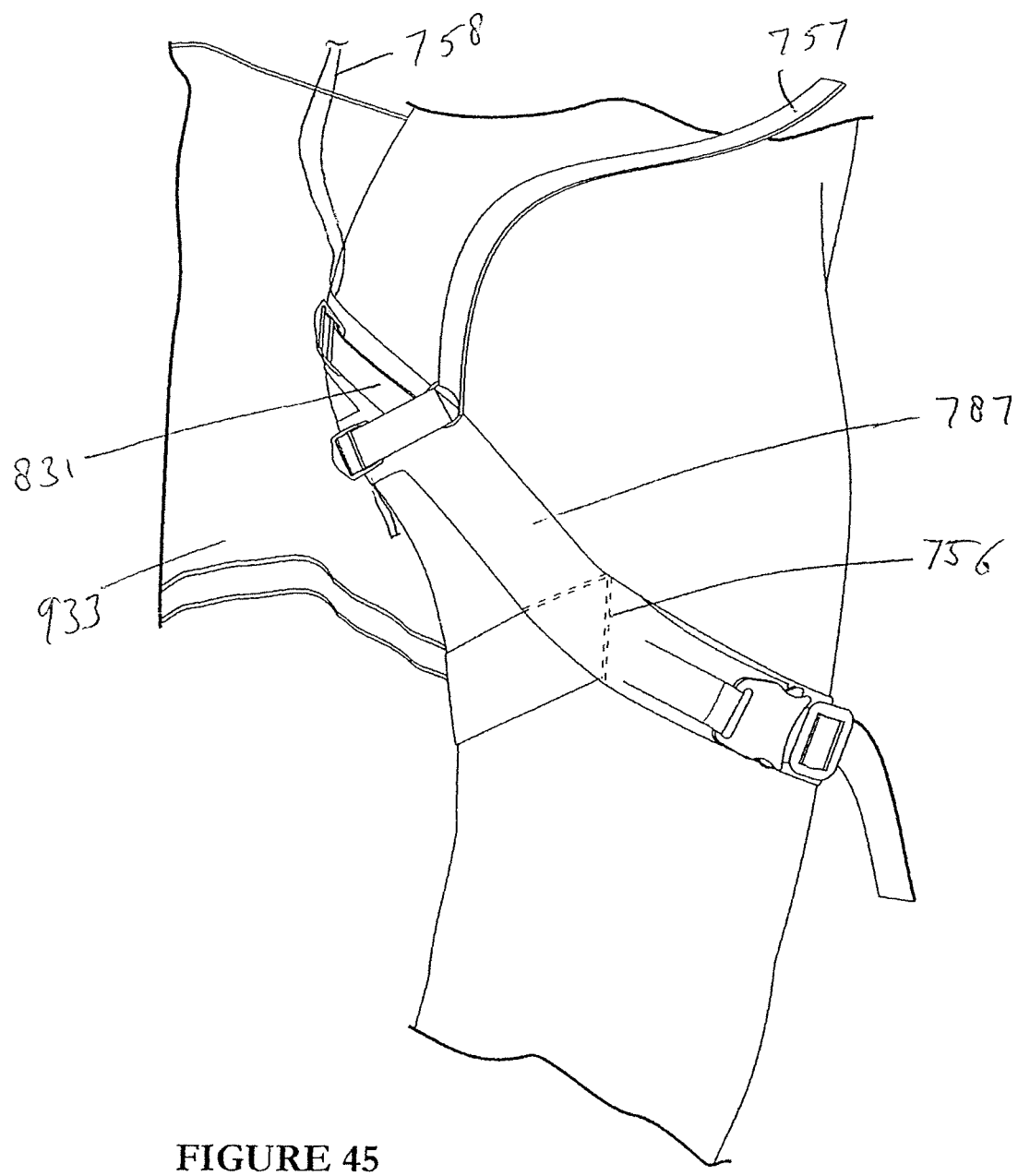
FIG. 45 shows a cutaway and partial view of FIG. 44.
Figure 46:
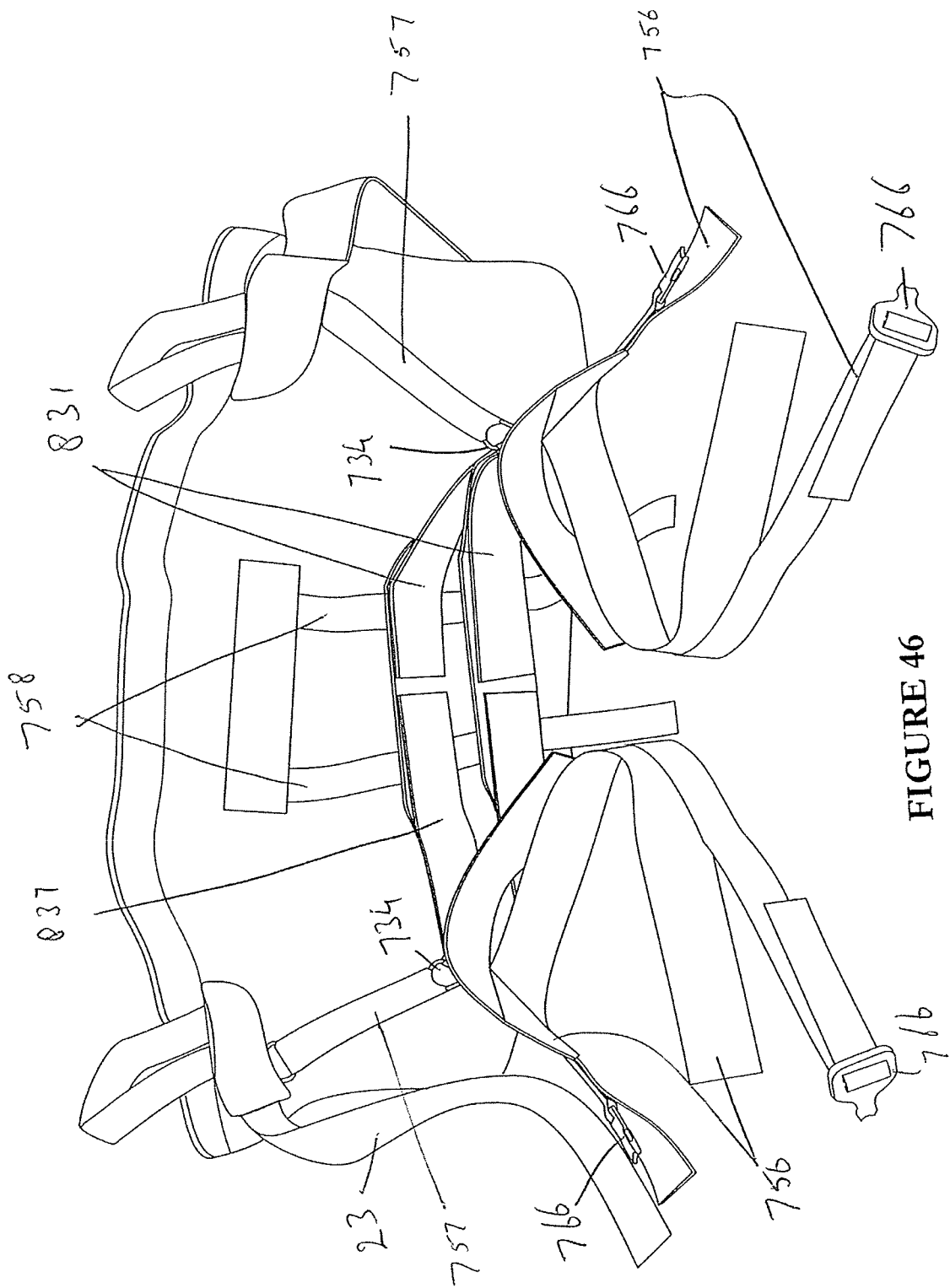
FIG. 46 shows a front view of the support harness.
Figure 47:
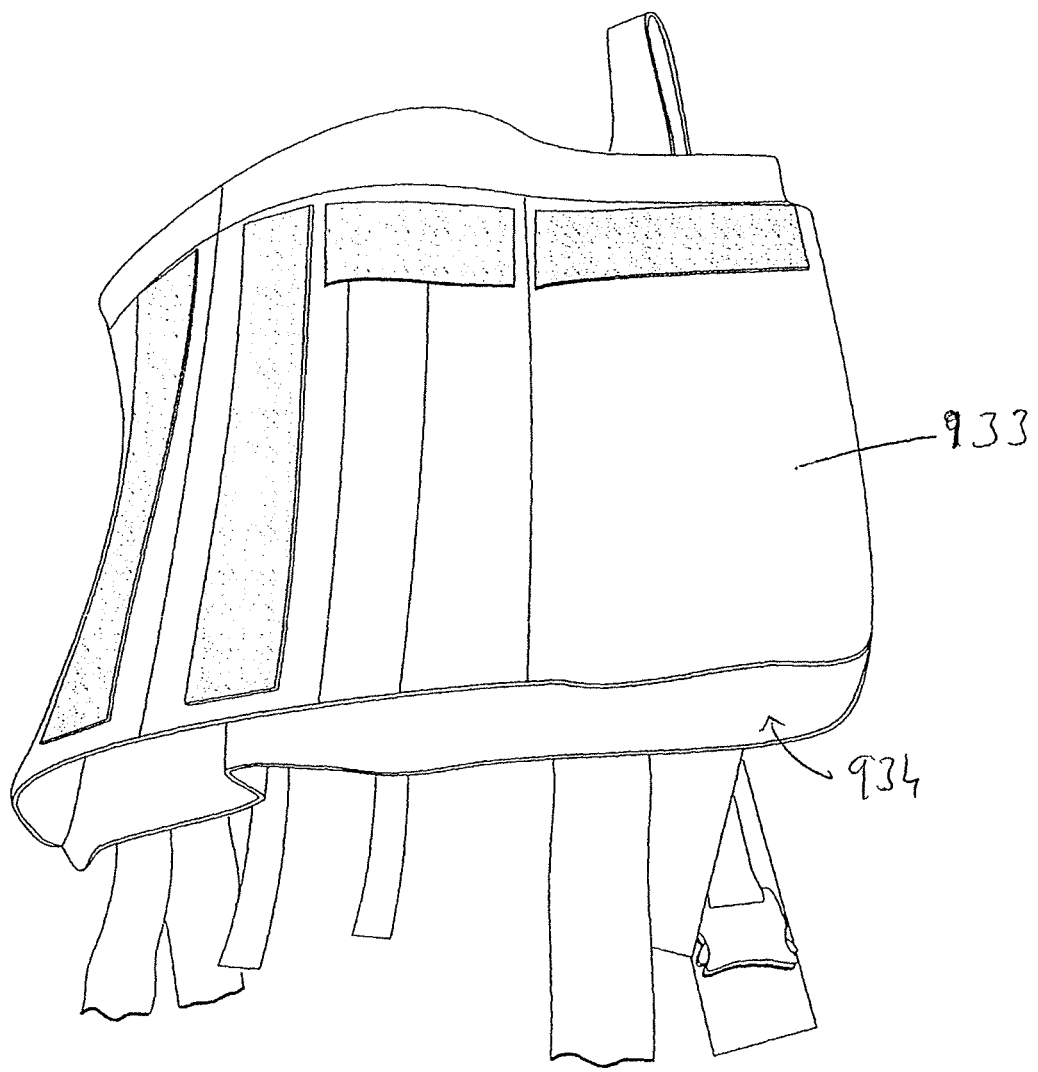
FIG. 47 shows a rear perspective view of the support harness and associated spacer.
Figure 48:
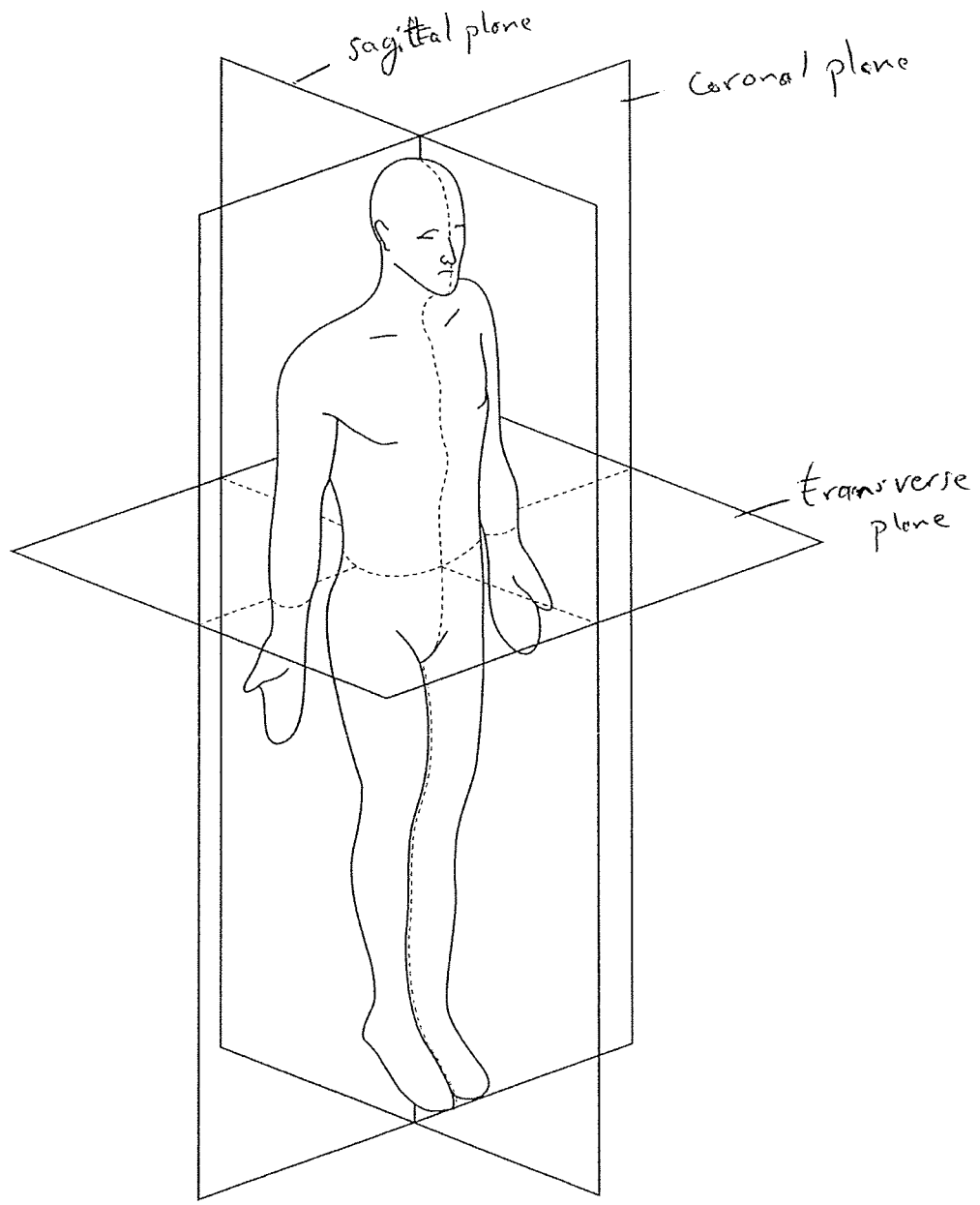
FIG. 48 shows a reference frame diagram.

FIGS. 44 to 47 show a pelvic support harness in more detail that helps support a user relative to the pelvic support member in a manner that is comfortable and of a nature to reduce any skin damage. The harness is predominantly made from webbing straps as shown in FIGS. 45 and 46. Suspension straps 757 are at or towards their upper ends fastened to the pelvic support member at points 821 as shown in FIG. 39 (shown on one side of the pelvic support member only). These suspension straps transfer most of the weight of the user to the pelvic support member 15. Dependent from the suspension straps 758 and 757 are the buttock straps 831 and the thigh straps 756.

The buttock straps comprise of a lower and upper buttock strap that form a cradle like shape to receive the buttocks of the user. The upper buttock strap 837 locates more around the posterior of the buttocks. The lower buttock strap is more proximate to the coronal plane. The upper and lower buttock straps can be adjusted in height relative to the pelvic support member by being moveably mounted relative to the suspension straps 758. They can also be adjusted in height at where they engage with the suspension straps 757.

The buttock straps can also be moved towards and away from each other by movement along the suspension traps 758 in order to change the shape of the cradle they form. The distance between suspension points 734 can also be adjusted by virtue of the buttock straps being length adjustable.

The thigh straps 756 are able to open and close by use of buckles 766. These can be adjusted to ensure a snug fit of the thigh straps to the user.

The thigh straps are designed to sit low around the inside leg of the thigh. And extend upwardly around to the other side of the thigh from there. The take-off strap 787 of the thigh strap is located on the outside of the leg and the load transferred there through helps locate the thigh strap relative the tight of the user in a manner to avoid the thigh strap from riding upwardly and into the crotch of the user.

Located intermediate of the harness and the pelvic support member is a spacer 933 that defines a pocket or pockets that removably contain spacer elements such as foam or inflatable pads. These are located in the pockets to pad out the gap between the user and the pelvic support member in order to ensure that a snug location of the user occurs relative to the pelvic support member.

Some or all of the components of the exoskeleton 500 may be fully or partially covered by covers 98 (as shown in FIGS. 14, 23, 25 and 38). These covers 98 are provided for safety, waterproofing, dustproofing and aesthetic purposes and said covers 98 will be of sufficient strength and stability to allow the user 600 to transfer into and out of the walker by using the covers for support. In one embodiment, handles may be built into the covers 98, to facilitate transfer of the user 600 to and from the exoskeleton 500.

Figure 40:
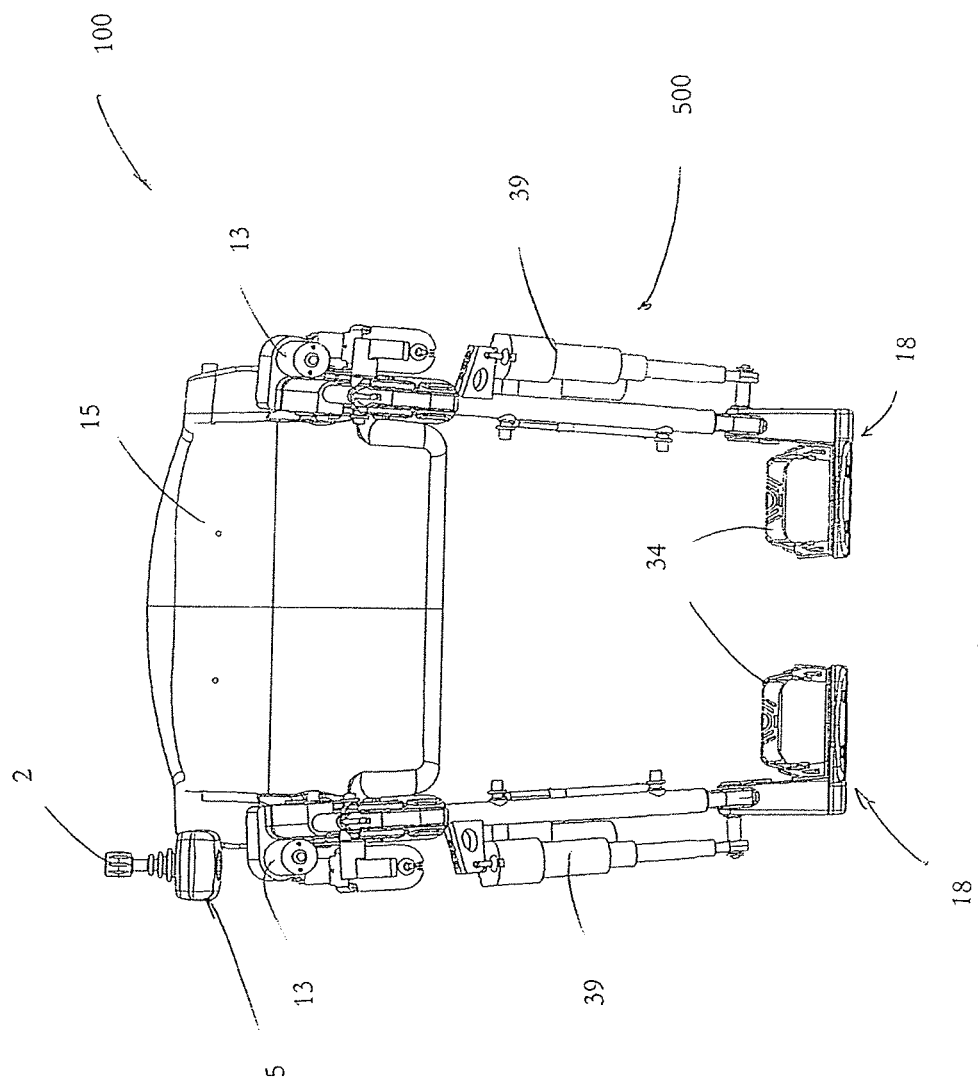
Figure 41:
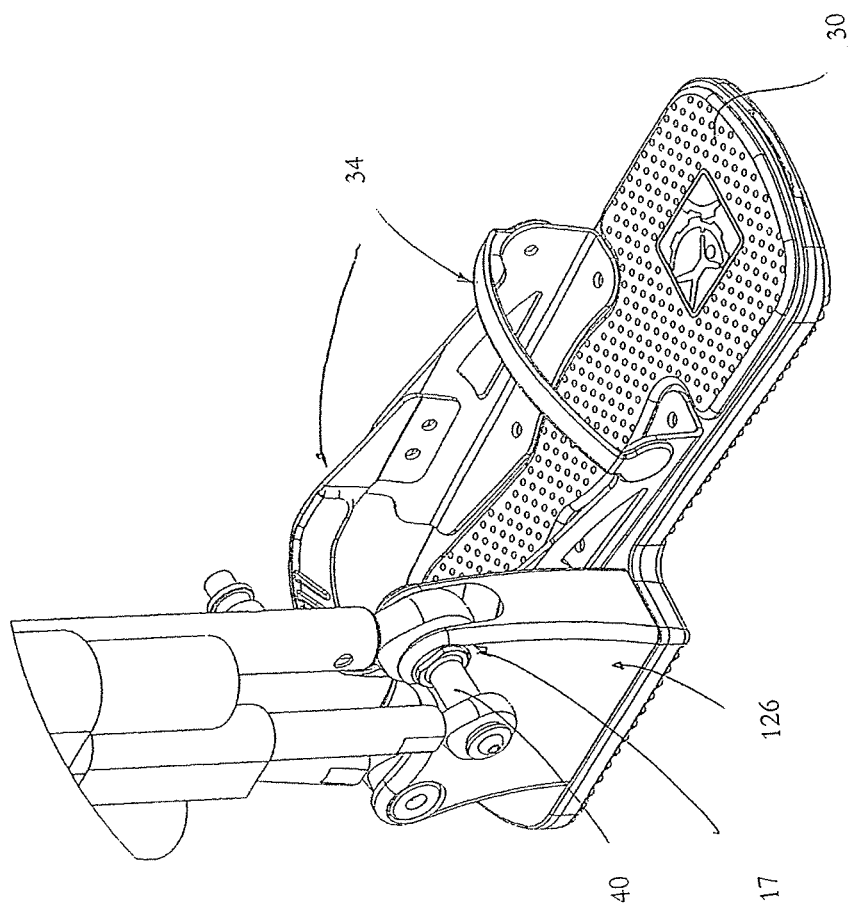
Figure 42:
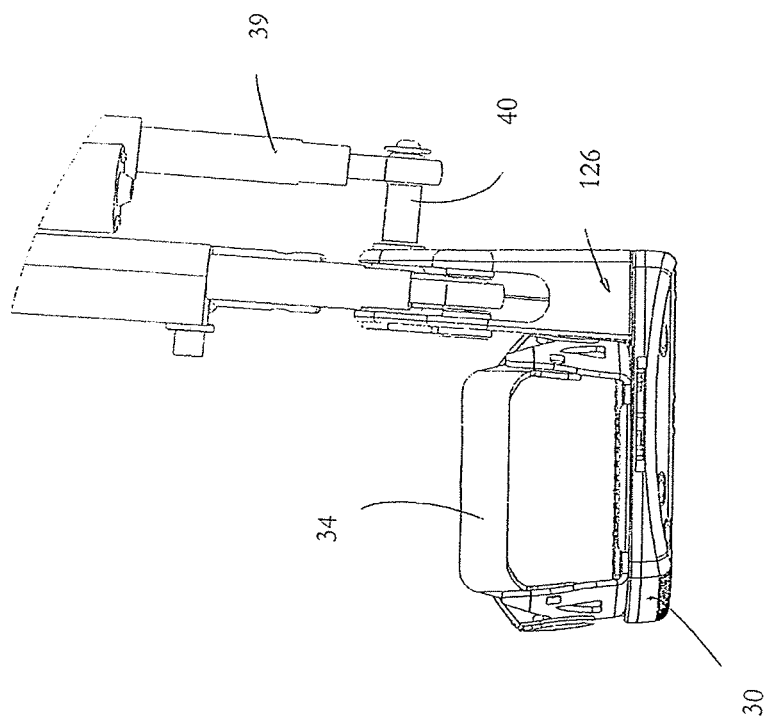
FIG. 42 shows a front view of a region near the foot joint of a walker.

In one embodiment, the exoskeleton 500 is configurable to a seated position (as shown in FIGS. 39 and 40). For example, when the exoskeleton 500 is in a seated position, the surfaces 99 of the covers (eg shown in FIG. 23, but not in the seated position) will extend substantially horizontally. The walker 100, located on a seat will then give the user a rigid surface to rely on for the purposes of their transfer into and out of the device. As such the covers 98 are preferably engaged to the exoskeleton in a rigid manner and in a manner that ensures they are stable relative thereto. The covers 98 may also (or instead) include functional shape features that can offer hand holds to the user for similar purposes.

The walker 100 may include a number of inertia measurement units 55 shown in FIGS. 9 and 10. Preferably, each of these inertia measurement units 55 may consist of an accelerometer, a gyroscope and an inclinometer. These inertia measurement units 55 measure and provide feedback on the attitude and rate of change of attitude and momentum of the walker 100 in operation and provide input variables to the controller.

It is envisaged that in one embodiment, the walker 100 can include distance sensors such as ultrasonic, laser or infrared sensors 56. These sensors can measure the distance between a set-point on the device to the surface of the ground. There may also be six ultrasonic sensors (not shown) to achieve this, one to the left, one to the right, one to the left side, one to the right side one at the back and one at the front of the device.

The walker 100 can also include two position sensors 58, 59 (ultrasonic, infrared or laser) at the front and two 60, 61 at the back of the device for detecting objects which could act as an obstacle to movement of the walker 100. The walker further includes a distance sensor on each leg measuring distance downwardly in front of each leg to potentially measure the distance from the lowest level of each foot to the ground or top of a step.

Figure 11:
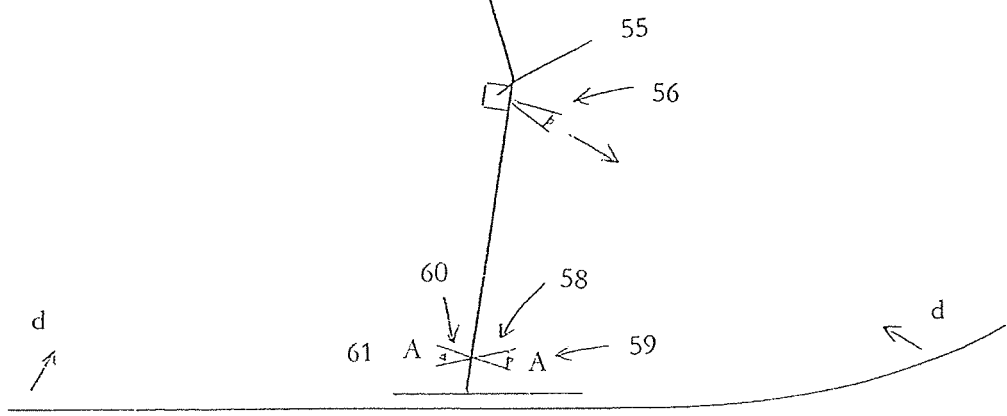
FIG. 11 shows a schematic side view of part of the exoskeleton showing sensors placement and their intended sensing of the surrounding environment.
Figure 13:
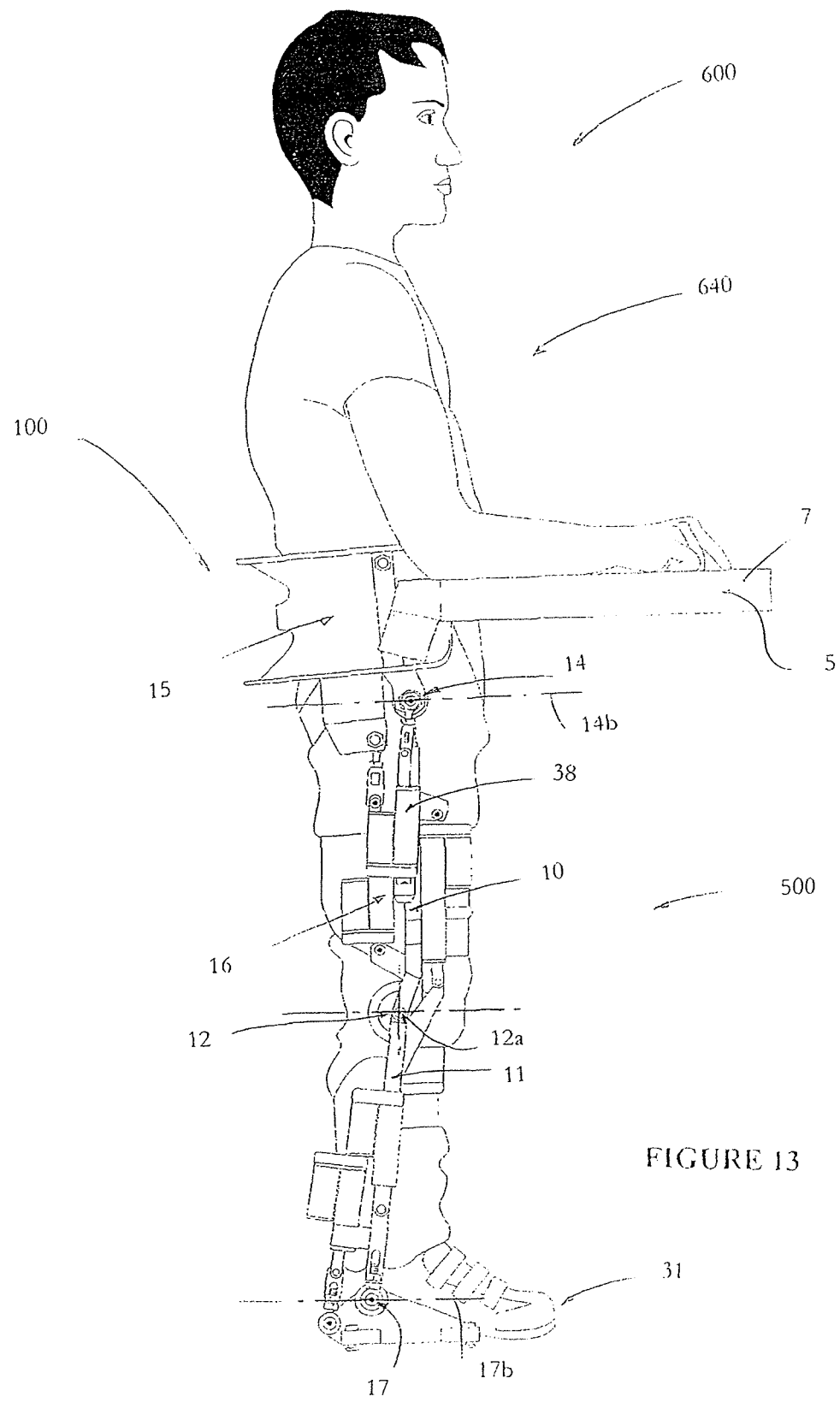
FIG. 13 is a side view of a person being supported by an embodiment of the walker including a secondary hip actuator.
Figure 14:
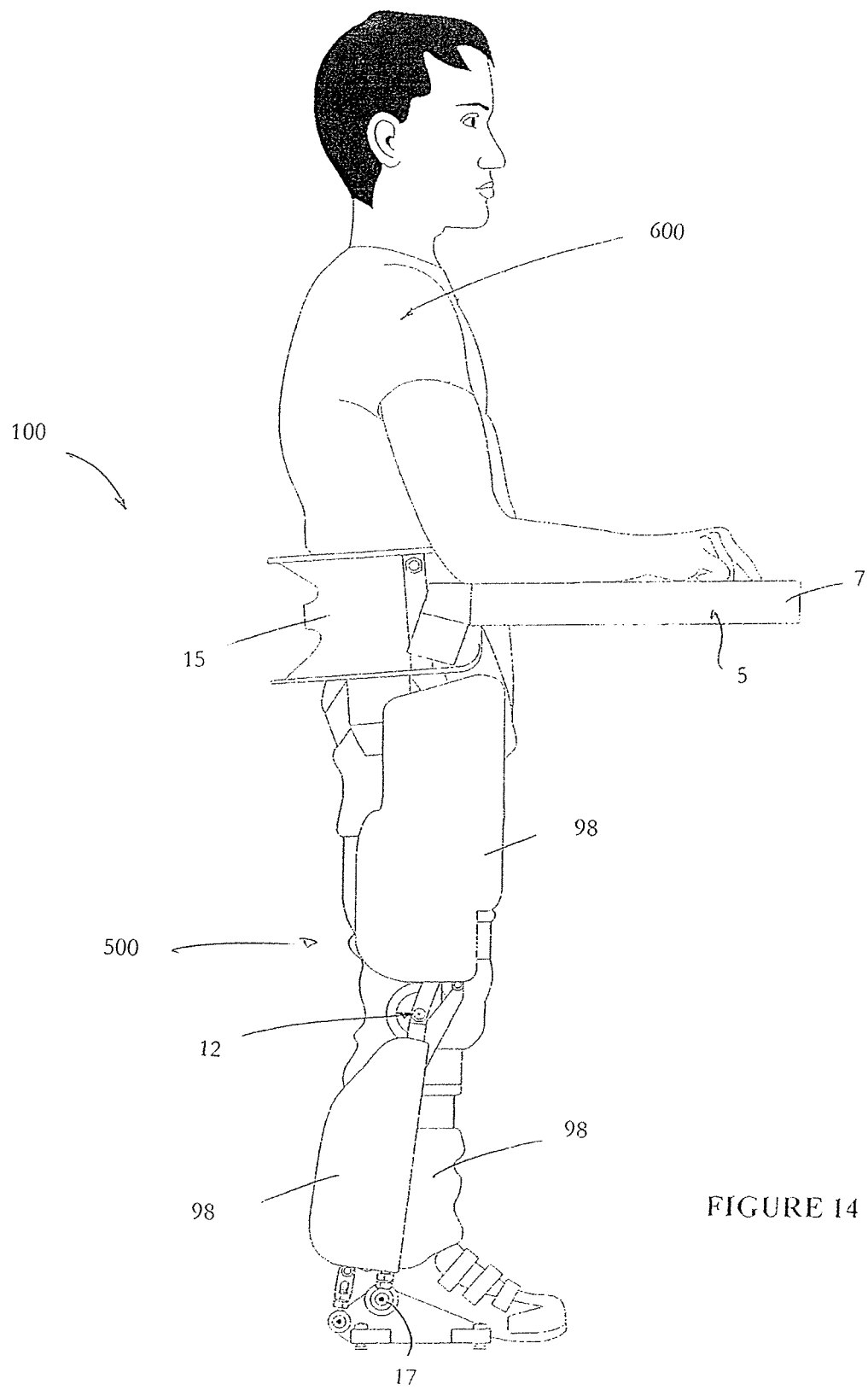
FIG. 14 shows a side view of a person supported by a walker with covers attached to it.
Figure 15:
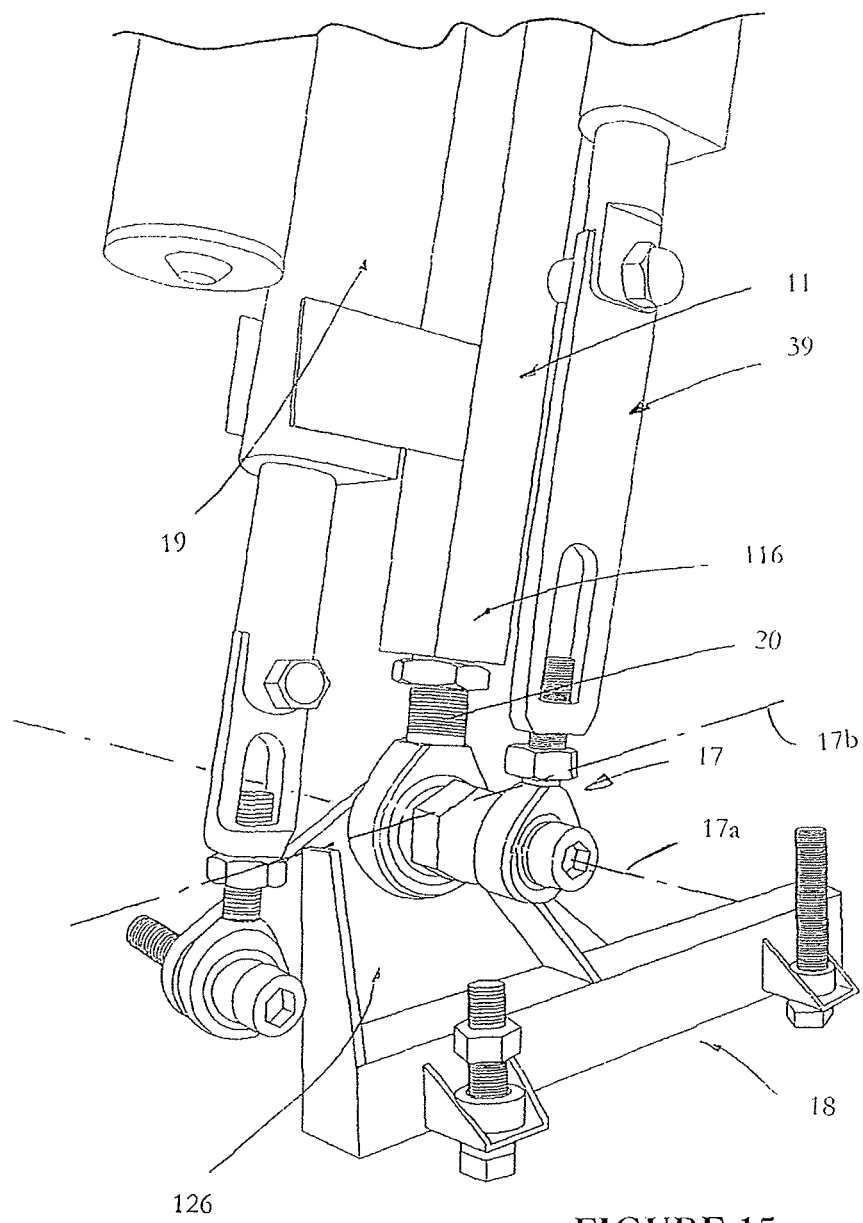
FIG. 15 shows a perspective cutaway rear view of the foot member and lower leg structural member of the exoskeleton.

In one embodiment, the foot member 18 can include contact/pressure sensors 67, 68, 69 (shown in FIG. 11) that can detect contact of the foot member 18 with a surface and/or the degree of pressure being applied by part of the foot member 18 to the surface, or even the pressure variation applied to the ground across the bottom of the foot member 18. It is envisaged that in a preferred embodiment, the sensors on the foot member 18 are sealed by a waterproof cover (not shown).

It is envisaged that any of these sensors are configurable for providing information to the control system for facilitating the control of movement of the exoskeleton 500. They will typically do this by sensing a particular characteristic to be sensed and generating a signal indicative of that characteristic, and transmitting the signal to the control system for facilitating the control of movement of the exoskeleton 500.

The device may also include seat sensors (not shown) for detecting forces applied by a user to the walker. It is envisaged that these could be in the form of a strain gauge (not shown) or the like. Two of these may exist at the rear of the walker 100, one in each "thigh" region.

The walker can further include pressure sensors 65 and 66 in the front and rear of the foot. These can detect any obstacles in front of the foot members 18.

It is envisaged that the walker control system (not shown) is configured to receive user input via a human interface device 1601 through which a human interface with the control system and may input information and receive information through sensory signals such as sound, light or vibration. Some examples of such a human interface device are a control pad (not shown), a keypad 3, a joystick 2, a touch screen or the like.

The control system includes a human interface device 1601. As described, various sensors, including sensors in the actuators are configurable to provide feedback signals which can be used by the control system for facilitating the control of the actuators.

In the preferred embodiment a control pad 4 will be used for human-machine interfacing. The control pad will be pivotable on a swing arm 5. It is envisaged that in one preferred embodiment, the control pad 7 contains a membrane keypad (3), light emitting diode (LED) lights (not shown), a joystick 2 and a battery meter (not shown). Other suitable human machine interfacing controls may be used. For example a touch screen (not shown) may replace the control pad.

The keypad 3 of the preferred embodiment may further include an audible buzzer to indicate warnings and the selection of inputs and/or functions of the control system.

It is envisaged that the LEDs can be used for a wide variety of functions, including fault indication, to indicate charging of the power supply, or to indicate that the emergency power supply (not shown) is being used.

The LED's can also be used as a battery meter to provide an indication of the available power in the main battery pack, ranging from all LEDs lit up meaning the battery is fully charged to no LEDs lit up meaning the battery needs charging.

The joystick 2 will be used as a user input means to input control instructions to the control system.

The walker is powered by on-board battery packs (not shown). In the preferred embodiment the battery packs are located at the 'kidneys' in the hip frame and at the front of the 'shins' in the leg covers 98. The battery system is a low voltage DC system and the battery packs are rechargeable from domestic power supply or vehicle power supplies. At least the actuators require power from the battery packs in order to allow them to actuate.

The battery packs are removable for quick replacement with another battery pack of similar capacity or extended capacity.

The battery packs can be charged on-board the walker or externally in the specifically designed charger.

Typically only a section of the battery packs will be used and in the event of these being depleted an audible alarm will sound as well as a visual battery charge indicator on the control panel will alert the user of the low battery power situation, the walker will then be able to automatically switch the power over to the reserve battery portion. Alternately, and in another preferred embodiment, the control panel will merely alert the user of a low power situation, and no reserve battery packs will be provided to conserve weight. It is envisaged that the walker 100 will assist in restoring basic mobility to a disabled user.

The walker is self contained with on board power and control systems and can be recharged using an in car charger or domestic power supply.

The invention claimed is:

1. A self contained powered exoskeleton walker for a disabled user that at least substitutes fully disabled functions of a user required for walking, said walker comprising:
   an exoskeleton comprising:
   a rigid pelvic support member including a user securing arrangement for securely fastening the user to at least the pelvic support member to fully support said user operationally at or towards a pelvic region of the user, so that the user's legs do not support the weight of the user,
   a first leg structure and a second leg structure, each of the first leg structure and the second leg structure being coupled to and extending from said pelvic support member for operational location adjacent a respective leg of the user, each of the first leg structure and second leg structure comprising
   an upper leg structural member for engagement with the upper leg of the user, the upper leg structural member being pivotally engaged at a first end thereof to the pelvic support member by a passive hip joint, wherein the hip joint is configured to be driven and for facilitating multi axis rotational movement of said upper leg structural member relative to said pelvic support member
   towards and away from a coronal plane of the user's body, and
   towards and away from a sagittal plane of the user's body for adduction and abduction;
   a lower leg structural member for engagement with the lower leg of the user, the lower leg structural member being pivotally engaged at a first end thereof to a second end of the upper leg structural member by a knee joint providing an axis of rotation,
   a foot member for engagement with a foot of the user, the foot member being pivotally engaged to at second end of the lower leg member by a foot joint,
   a linear main hip actuator configured for actuating pivotal movement and control the position of said upper leg structural member relative to said pelvic support member about said hip joint; to in use pivot the upper leg structural member towards and away from the coronal plane of the body of the user, the main hip actuator connected at
   i) a proximal end to the pelvic support member at an offset distance below and posterior to the pivotal axis of the hip joint and
   ii) a distal end to the upper leg structural member at an offset distance above the knee joint, a linear secondary nip actuator, configured for actuating pivotal movement and control the position of said upper leg structural member relative the pelvic support member about said hip joint towards and away from the sagittal plane of the body of the user for adduction and abduction, the secondary hip actuator connected at
   i) a proximal end to the pelvic support member at an offset distance collinear to the pivotal axis of the hip joint and
   ii) a distal end to the upper leg structural member at an offset distance posterior of the knee joint,
   a knee actuator configured for actuating pivotal movement and control the position of said lower leg structural member relative said upper leg structural member about said knee joint,
   a main foot actuator configured for actuating pivotal movement and controlling the position of said foot member relative said lower leg structural member,
   a power source configurable for providing power to at least one or more selected, from said main hip actuators, knee actuators, and main foot actuators,
   a control system configurable for controlling movement of at least one or more actuators selected from said main and secondary hip actuators, knee actuators, and main foot actuators, thereby to move the exoskeleton relative to ground on which the walker is positioned, for at least the purposes of effecting a walking motion to said user;
   wherein the control system is configured to receive a user input via a human interface device to input control instructions to the control system to control movement of said at least one or more actuators, and wherein the human interface device comprises at least one of: a control pad, a keypad, a joystick, and a touch screen; and
   wherein the human interface device is configured to generate sound or light information to convey a system state of the walker to the user.

2. The walker as claimed in claim 1, wherein said secondary hip actuator is configured for actuating said pivotal movement of said upper leg structural member to either side of a plane parallel to the sagittal plane and passing through said hip joint.

3. The walker as claimed in claim 1, wherein said hip joint is one selected from a rose joint, universal joint or bail and socket joint, configured for facilitating a multi axis rotational capability of said upper leg structural member relative to said pelvic support member.

4. The walker as claimed in claim 1, wherein pivotal movement of the upper leg structural member by the main hip actuator is about an axis of rotation extending laterally from said sagittal plane and downwardly at an angle of between 1 and 6 degrees to the transverse plane.

5. The walker as claimed in claim 1, wherein the knee joint is offset rearwardly from the upper leg structural member to align substantially with an axis of rotation of the user's knee in operation.

6. The walker as claimed in claim 1, wherein the knee joint is a polycentric knee joint.

7. The walker as claimed in claim 1, wherein said foot joint is a rose joint, a universal joint or ball and socket joint, configured for facilitating multi axis rotational capability of said foot member relative said lower leg structural member.

8. The walker as claimed in claim 1, wherein said exoskeleton comprises, for each of the first leg structure and second leg structure, a secondary foot actuator, configured for actuating rotation of said foot member about an axis of rotation extending parallel to said sagittal plane.

9. The walker as claimed in claim 1, wherein each foot joint is configured for pivotal movement of the foot member by the main foot actuator with the axis of the foot joint extending laterally of the sagittal plane and downwardly at an angle of between zero and 6 degrees to the transverse plane.

10. The walker as claimed in claim 1, wherein the foot joint is configured for pivotal movement of the foot member by the secondary foot actuator in a range of about six degrees to either side of a vertical plane.

11. The walker as claimed in claim 1, wherein a plurality of sensors are provided for providing information to the control system for facilitating control of movement of the exoskeleton.

12. The walker as claimed, in claim 11, wherein the plurality of sensors are configured for sensing a characteristic to be sensed, and generating a signal indicative of that characteristic, and transmitting the signal to the control system for facilitating the control of movement of the exoskeleton.

13. The walker as claimed in claim 11, wherein said sensors are selected from at least one of:
    an accelerometer to measure an acceleration of at least one or more selected from said pelvic support member, the upper leg structural members, the lower leg structural members and the foot members,
    an inclinometer to measure an inclination of at least one or more selected from said pelvic support member, the upper leg structural members, the lower leg structural members and the foot members,
    distance sensors configured for determining a slope of the ground anteriorly, posteriorly and laterally of the walker,
    pressure sensors disposed on the foot member to determine pressure being applied by the foot member to the ground, and
    position sensors for determining position and velocity of the actuators.

14. The walker as claimed in claim 1, wherein said controller includes a gyroscope configured for defining a reference frame for purposes of positional control of the exoskeleton or part of the exoskeleton.

15. The walker as claimed in claim 1, wherein the user securing arrangement includes a harness configured and adapted for securely fastening the user to the at least one pelvic support member.

16. The walker as claimed in claim 1, further comprising one or more covers for covering one or more components of the exoskeleton, wherein the one or more covers are configured to support the user when transferring into and out of the walker.

17. The walker as claimed in claim 1, wherein the human interface device is repositionable between an in-use position and a not in-use position.

18. The walker as claimed in claim 1, further comprising a distance sensor for measuring a distance between a location of the distance sensor on the exoskeleton and a ground surface.

19. The walker as claimed in claim 1, further comprising a position sensor for detecting a position of an object that may act as an obstacle to movement of the walker.

20. An exoskeleton device worn by a paraplegic user for device controlled walking of the user, said exoskeleton device comprising:
    a rigid pelvic support member including a user securing arrangement for engaging with the user at or towards the pelvis of the user to fully support said user operationally so that the user's legs do not support the weight of the user,
    a first leg structure and a second leg structure, each of the first leg structure and the second leg structure being coupled to and extending from said pelvic support member for operational location adjacent a respective leg of a user, each of the first leg structure and second leg structure comprising
    an upper leg structural member for engagement with the upper leg of the user, the upper leg structural member being pivotally engaged at a first end thereof to the pelvic support member by a hip joint, wherein the hip joint is configured for facilitating multi axis rotational movement of said upper leg structural member relative to said pelvic support member towards and away from the user's coronal plane in operation;
    a lower leg structural member for engagement with the lower leg of the user, the lower leg structural member being pivotally engaged at a first end thereof to a second end of the upper leg structural member by a knee joint,
    a foot member for engagement with the root of a user, the foot member being pivotally engaged to a second end of the lower leg member by a passive foot joint configured to be driven and for facilitating multi axis rotational movement of said foot member relative to said lower leg member
    towards and away from a transverse plane of the user's body for dorsiflexion and plantar flexion of the foot member, and towards and away from a sagittal plane of the user's body for inversion and eversion of the foot member,
    a main hip actuator configured for actuating pivotal movement and control the position of said upper leg structural member relative to said pelvic support member about said hip joint, to in use pivot the upper leg structural member towards and away from the coronal plane of the body of the user,
    a knee actuator configured for actuating pivotal movement and control the position of said lower leg structural member relative said upper leg structural member about said knee joint,
    a linear main foot actuator configured for actuating pivotal movement and controlling the position of said, foot member relative said lower leg structural member for dorsiflexion and plantar flexion about said foot joint, the main foot actuator connected at
    i) a proximal end to the foot member at an offset distance below and posterior to the pivotal axis the foot joint and
    ii) a distal end to the lower leg structural member at an offset, distance below and, posterior to the knee joint;
    a linear secondary foot actuator configured for actuating pivotal movement and control the position of said foot member relative said, lower leg structural member for inversion and eversion of the foot member about said foot, joint, the secondary foot actuator connected at
    i) a proximal end to the foot member at an offset distance below and posterior to the pivotal axis of the foot joint, and
    ii) a distal end to the lower leg structural member at an offset distance below and posterior to the knee joint; and
    a control system configurable for controlling movement of at least one or more actuators selected from said main hip actuator, knee actuator, and main and secondary foot actuators, thereby to move the exoskeleton relative to ground on which the walker is positioned, for at least the purposes of effecting a walking motion to said user,
    wherein the control system is configured to receive a user input via a human interface device to input control instructions to the control system to control movement of said at least one or more actuators, and wherein the human interface device comprises at least one of: a control pad, a keypad, a joystick, and a touch screen; and
    wherein the human interface device is configured to generate sound or light information to convey a system state of the exoskeleton to the user.

21. The exoskeleton device as claimed in claim 20, wherein said exoskeleton comprises a power source configurable for providing power to at least one or more selected from said main hip actuators, knee actuators, and main foot actuators.

22. The exoskeleton device as claimed in claim 20, wherein the exoskeleton device is worn by a paraplegic user for device controlled and user specified walking motion.

23. The exoskeleton device as claimed in claim 20, wherein the actuators are electric actuators.

24. The exoskeleton device as claimed in claim 20, wherein the foot joint is a rose joint.

25. The exoskeleton as claimed in claim 20, wherein the user securing arrangement includes a harness configured and adapted for securely fastening the user to the at least one pelvic support member.

26. The exoskeleton as claimed in claim 20, further comprising one or more covers for covering one or more components of the exoskeleton, wherein the one or more covers are configured to support the user when transferring into and out of the exoskeleton.

27. The exoskeleton as claimed in claim 20, wherein the human interface device is repositionable between an in-use position and a not in-use position.

28. The exoskeleton as claimed in claim 20, further comprising a distance sensor for measuring a distance between a location of the distance sensor on the exoskeleton and a ground surface.

29. The exoskeleton as claimed in claim 20, further comprising a position sensor for detecting a position of an object that may act as an obstacle to movement of the exoskeleton.

\* \* \* \* \*

UNITED STATES PATENT AND TRADEMARK OFFICE
CERTIFICATE OF CORRECTION

| | |
|---|---|
| PATENT NO. | : 11,185,460 B2 |
| APPLICATION NO. | : 14/850349 |
| DATED | : November 30, 2021 |
| INVENTOR(S) | : Little et al. |

It is certified that error appears in the above-identified patent and that said Letters Patent is hereby corrected as shown below:

On the Title Page

Item (63), Related U.S. Application Data: should read:
(63) Continuation of application No. 12/801,809 filed on June 25, 2010, now abandoned, which is a continuation-in-part of PCT/NZ08/00351 filed on December 24, 2008, which claims benefit of U.S. Provisional Application No. 61/006,136 filed on December 26, 2007

Signed and Sealed this
Seventeenth Day of May, 2022

*Katherine Kelly Vidal*

Katherine Kelly Vidal
*Director of the United States Patent and Trademark Office*